US007763687B2

(12) United States Patent
Ober et al.

(10) Patent No.: US 7,763,687 B2
(45) Date of Patent: Jul. 27, 2010

(54) POLYMERS CONTAINING QUATERNIZED NITROGEN

(75) Inventors: Christopher K. Ober, Ithaca, NY (US); Sitaraman Krishnan, Ithaca, NY (US); Qin Lin, Ithaca, NY (US); Edward Kramer, Santa Barbara, CA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 957 days.

(21) Appl. No.: 11/507,361

(22) Filed: Aug. 21, 2006

(65) Prior Publication Data

US 2007/0106040 A1 May 10, 2007

Related U.S. Application Data

(63) Continuation-in-part of application No. 11/063,242, filed on Feb. 22, 2005.

(60) Provisional application No. 60/709,925, filed on Aug. 19, 2005, provisional application No. 60/546,656, filed on Feb. 20, 2004.

(51) Int. Cl.
*C08F 4/44* (2006.01)
*C08F 4/72* (2006.01)

(52) U.S. Cl. .................................................. 526/110

(58) Field of Classification Search ........................ None
See application file for complete search history.

(56) References Cited

U.S. PATENT DOCUMENTS

| 4,011,178 | A | 3/1977 | Muse |
| 4,480,075 | A | 10/1984 | Willis |
| 4,659,785 | A | 4/1987 | Nagano et al. |
| 5,336,717 | A | 8/1994 | Rolando et al. |
| 5,907,017 | A | 5/1999 | Ober et al. |
| 6,114,467 | A | 9/2000 | Ober et al. |
| 6,583,228 | B2 | 6/2003 | Nkansah et al. |
| 6,750,296 | B2 | 6/2004 | Ober et al. |
| 2006/0083854 | A1 | 4/2006 | Ober et al. |
| 2007/0053867 | A1 | 3/2007 | Ober et al. |

FOREIGN PATENT DOCUMENTS

JP 2002/105152 4/2002

OTHER PUBLICATIONS

Ober et al., {Block copolymers as surface modifiers: Synthesis, characterization and relevance to fouling release and biostability, PMSE Preprints (2003), 88, 612-613}.*
Zhu et al., {Interfacial behavior of block polyelectrolytes. 6. Properties of surface micelles as a function of R and X in P(S260-b-VP240/RX), Macromolecules (1992), 25(24), 6556-62}.*
"Barnacle Free Boats", *ScienCentral News*, (Observed Feb. 28, 2005), 3 pgs.
"DuPont™ Zonyl® FSO—Fluorosurfactant", *Dupont Technical Information Sheet* (P-200125.8), (2002), 2 pgs.
"DuPont™ Zonyl® FSN—Fluorosurfactant", *Dupont Technical Information Sheet* (P-200125.8), (2002), 2 pgs.
"DuPont™ Zonyl® FSN-100—Fluorosurfactant", *Dupont Technical Information Sheet* (P-200125.8), (2002), 2 pgs.
"DuPont™ Zonyl® FSO-100—Fluorosurfactant", *Dupont Technical Information Sheet* (P-200125.8), (2002), 2 pgs.
Baier, R. E., "Influence of the Initial Surface Condition of Materials on Bioadhesion", (Published Prior to Sep. 22, 2005), 633-639.
Callow, M. E., et al., "Microtopographic Cues for Settlement of Zoospores of the Green Fouling Alga *Enteromorpha*", *Biofouling*, 18(3), (2002) ,237-245.
Callow, M. E., et al., "Primary Adhesion of *Enteromorpha* (Chlorophyta, Ulvales) Progagules: Quantitative Settlement Studies and Video Microscopy", *J. Phycol.*, 33, (1997), 938-947.
Callow, M. E., et al., "The Influence of Low Surface Energy Materials on Bioadhesion—a Review", *International Biodeterioration & Biodegradation*, (1994), 333-348.
Callow, M. E., et al., "Use of Self-Assembled Monolayers of Different Wettabilities to Study Surface Selection and Primary Adhesion Processes of Green Algal (*Enteromorpha*) Zoospores", *Applied and Environmental Microbiology*, 66(8), (2000), 3249-3254.
Davis, K. A., "ABC Triblock Copolymers Prepared Using Atom Transfer Radical Polymerization Techniques", *Macromolecules*, 34(7), (2001), 2101-2107.
Fields, S. , et al al., "New Paint: No Harm, No Foul?", *Environmental Health Perspectives*, 111(9), (2003), p. A457.
Finlay, J. A., et al., "Adhesion Strength of Settled Spores of the Green Alga *Enteromorpha*", *Biofouling*, 18(4), (2002), 251-256.
Finlay, J. A., et al., "The Influence of Surface Wettability on the Adhesion Strength of Settled Spores of the Green Alga *Enteromorpha* and the Diatom *Amphora*", *Integr. Comp. Biol.*, 42, (2002), 1116-1122.
Freij-Larsson, C., et al., "Adsorption Behaviour of Amphiphilic Polymers at Hydrophobic Surfaces: Effects on Protein Adsorption", *Biomaterials*, 17(22), (Nov. 1996) , 2199-2207.
Gudipati, C. S., et al., "The Antifouling and Fouling-Release Performance of Hyperbranched Fluoropolymer (HBFP)-Poly(ethylene glycol)(PEG) Composite Coatings Evaluated by Adsorption of Biomacromolecules and the Green Fouling Alga *Ulva*", *Langmuir*, 21(7), (2005), 3044-3053.
Hexemer, A., et al., "Managing Polymer Surface Structure Using Surface Active Block Copolymers in Block Copolymer Mixtures", *Journal of Polymer Science Part B: Polymer Physics*, 42(3), (2003), 411-420.

(Continued)

*Primary Examiner*—Sikarl A Witherspoon
*Assistant Examiner*—Chukwuma O Nwaonicha
(74) *Attorney, Agent, or Firm*—Schwegman, Lundberg & Woessner P.A.

(57) ABSTRACT

The invention provides polymers, methods of preparing polymers, and compositions that include polymers, wherein said polymers include a plurality of two-carbon repeating units in a polymer chain, wherein one or more of the two-carbon repeating units of the polymer chain have tertiary amine or pyridine-containing substituents; and at least about 10% of the nitrogen atoms of the tertiary amine or pyridine-containing substituents are quaternized with alkyl groups or with an alkyl group that contains one or more ethylene glycol groups. The alkyl or ethoxylated alkyl groups can also be at least partially fluorinated. The polymers can be used to provide antimicrobial surfaces and antifouling coatings.

17 Claims, 15 Drawing Sheets

OTHER PUBLICATIONS

Hourdet, D., et al., "Synthesis of Thermoassociative Copolymers", *Polymer*, 38(10), (May 1997), 2535-2547.

Hussain, H., et al., "Amphiphilic Block Copolymers of Poly(ethylene oxide) and Poly(perfluorohexylethyl methacrylate) at the Water Surface and Their Penetration into the Lipid Monolayer", *J. Phys. Chem. B.*, 108(28), (2004), 9962-9969.

Keszler, B., et al., "Amphiphilic Networks—V. Polar/Nonpolar Surface Characteristics, Protein Adsorption From Human Plasma and Cell Adhesion", *Polymer Bulletin*, 29, (1992), 681-688.

Krishnan, S., et al., "Anti-Biofouling Properties of Comblike Block Copolymers With Amphiphilic Side Chains", *Langmuir*, 22, (2006), 5075-5086.

Krishnan, S., et al., "Antibacterial Coatings Based on Quaternized Poly(4-vinylpyridine) Block Copolymers", (Abstract Only), *PMSE Preprints*, 91, (2004), 1 pg.

Krishnan, S., et al., "Comparison of the Fouling Release Properties of Hydrophobic Fluorinated and Hydrophilic PEGylated Block Copolymer Surfaces: Attachment Strength of the Diatom *Navicula* and the Green Alga *Ulva*", *Biomacromolecules*, 7, (2006), 1449-1462.

Lee, S. B., et al., "Permanent, Nonleaching Antibacterial Surfaces. 1. Synthesis by Atom Transfer Radical Polymerization", *Biomacromolecules*, 5, (2004), 877-882.

Li, J., et al., "Synthesis of Polyethylene Glycol (PEG) Derivatives and PEGylated-Peptide Biopolymer Conjugates", *Biomacromolecules*, 4, (2003), 1055-1067.

Mao, G., et al., "Molecular Design, Synthesis, and Characterization of Liquid Crystal-Coil Diblock Copolymers with Azobenzene Side Groups", *Macromolecules*, 30, (1997), 2556-2567.

Masson, P., et al., "Thermotropic Liquid Crystalline Behaviour of Pyridinium and Poly(4-vinylpyridinium) Salts Quaternized With Ω-alkyl Phenylbenzoate Derivatives", *Macromolecular Chemistry and Physics*, 200(3), (1999) 616-620.

Ober, C. K., et al., "Surface-Active Materials With Antifouling Properties", *Polymer Preprints*, 45(1), (2004), 2 pgs.

Ostuni, E., et al., "Self-Assembled Monolayers That Resist the Adsorption of Proteins and the Adhesion of Bacterial and Mammalian Cells", *Langmuir*, 17, (2001), 6336-6343.

Park, D., et al., "Amphiphilic Networks. 9. Surface Characterization", *Macromolecules*, 28(8), (1995), 2595-2601.

Poe, G. D., et al., "Enhanced Coil Expansion and Intrapolymer Complex Formation of Linear Poly(methacrylic acid) Containing Poly(ethylene glycol) Grafts", *Macromolecules*, 37(7), (2004), 2603-2612.

Sigal, G. B., et al., "Effect of Surface Wettability on the Adsorption of Proteins and Detergents", *J. Am. Chem. Soc.*, 120, (1998), 3464-3473.

Swain, G. W., et al., "The Influence of Biofouling: Adhesion and Biotic Disturbance on the Development of Fouling Communities on Non-Toxic Surfaces", *Biofouling*, 12(1-3), 1998, 257-269.

Tiller, J. C., et al., "Designing Surfaces That Kill Bacteria on Contact", *Proc. Natl. Acad. Sci. USA*, 98(11), (May 22, 2001), 5981-5985.

Vreeland, V., et al., "Polyphenols and Oxidases in Substratum Adhesion by Marine Algae and Mussels", *J. Phycol.*, 34, (1998), 1-8.

Wang, J., "Liquid Crystalline, Semifluorinated Side Group Block Copolymers with Stable Low Energy Surfaces: Synthesis, Liquid Crystalline Structure, and Critical Surface Tension", *Macromolecules*, 30(7), (Apr. 1997), 1906-1914.

Wang, J., et al., "Self-Organizing Materials With Low Surface Energy: The Synthesis and Solid-State Properties of Semifluorinated Side-Chain Ionenes", *Macromolecules*, 30(24), (1997), 7560-7567.

Wynne, K. J., et al., "Two Silicone Nontoxic Fouling Release Coatings: Hydrosilation Cured PDMS and $CaCO_3$ Filled, Ethoxysiloxane Cured RTV11", *Biofouling*, 16(2-4), (2000),277-288.

Xiang, M., "Surface Stability in Liquid-Crystalline Block Copolymers with Semifluorinated Monodendron Side Groups", *Macromolecules*, 33(16), (Aug. 2000), 6106-6119.

Youngblood, J. P., et al., "Coatings Based on Side-Chain Ether-Linked Poly(ethylene glycol) and Fluorocarbon Polymers for the Control of Marine Biofouling", *Biofouling*, 19 (Supplement), (2003), 91-98.

"U.S. Appl. No. 11/063,242, Response filed Nov. 19, 2008 to Non-Final Office Action mailed Aug. 19, 2008", 13 pgs.

"U.S. Appl. No. 11/063,242, Non-Final Office Action mailed Aug. 19, 2008", 8 pgs.

"U.S. Appl. No. 11/507,355 Restriction Requirement", 5.

"U.S. Appl. No. 11/063,242, Supplemental Amendment and Response filed Jan. 14, 2009 to Notice of Non-Compliant mailed Dec. 22, 2008", 10.

"U.S. Appl. No. 11/063,242, Non-Final Office Action mailed Apr. 1, 2009", 8 pgs.

"U.S. Appl. No. 11/063,242, Response filed Jul. 1, 2009 to Non Final Office Action mailed Apr. 1, 2009", 13 pgs.

"U.S. Appl. No. 11/507,355, Non-Final Office Action mailed Aug. 4, 2009", 14 Pgs.

Cormack, P., et al., "Molecular imprinting: recent developments and the road ahead", *Reactive and Functional Polymers*, 41(1-3), (Jul. 15, 1999), 115-124.

"U.S. Appl. No. 11/063,242 Notice of Allowance Mailed Dec. 14, 2009", 8 pgs.

"U.S. Appl. No. 11/507,355, Response filed Dec. 31, 2009 to Non Final Office Action mailed Aug. 4, 2009", 13 pgs.

* cited by examiner

US 7,763,687 B2

POLYMERS CONTAINING QUATERNIZED NITROGEN

RELATED APPLICATIONS

This application claims priority under 35 U.S.C. §119(e) to U.S. Provisional Patent Application No. 60/709,925, filed Aug. 19, 2005, and this application is also a continuation-in-part of U.S. patent application Ser. No. 11/063,242, filed Feb. 22, 2005, which claims priority under 35 U.S.C. §119(e) to U.S. Provisional Patent Application No. 60/546,656, filed Feb. 20, 2004, which applications are incorporated herein by reference.

GOVERNMENT SUPPORT

This invention was made with Government support under Grant Numbers N00014-02-1-0170 awarded by the Office of Naval Research and PP-1454 awarded by the Strategic Environmental Research and Development Program (SERDP) of the Department of Defense. The United States Government has certain rights in this invention.

BACKGROUND OF THE INVENTION

Marine fouling is a major problem in the transport of materials by sea as it can raise fuel consumption by as much as 30%. Environmentally friendly coatings that protect the hulls of ships below the waterline against fouling by seaweed, barnacles, and other organisms are currently sought by the shipping industry. Fouling by these organisms produces additional drag on the ship, thereby increasing operating and maintenance costs.

Antifouling paints containing tin and copper biocides are currently used because of their effectiveness against most forms of marine fouling. Many of these biocidal organometallic compounds are environmentally persistent. They can cause damage to the ecosystem and enter the food chain. The ban on tributyltin (TBT) antifoulants by the International Maritime Organization will be effective in 2008, and copper-based coatings are expected to face similar restrictions in the near future.

Non-toxic "fouling-release" or "fouling-repellant" coatings are one class of alternatives to biocidal coatings. Silicone-based paints are commercially available, but do not satisfy many desired performance characteristics. The soft silicones do not withstand the rigorous demands of the marine environment, do not sufficiently and consistently self-clean, or, due to polymer restructuring or other degradation pathways, lose many of the desirable surface properties with time and exposure to marine organisms.

Several fouling release (FR) coating systems are commercially available, mostly based on silicone polymers, yet none meet all of the desired performance characteristics. Many commercially available coating systems lack the toughness required to withstand the rigorous physical demands of the marine environment, do not sufficiently and consistently self-clean, and due to polymer restructuring or other degradation pathways, lose many of the desirable surface properties with time and exposure to the marine environment.

Current understanding of antifouling materials is that the most effective copper-free fouling control systems are low surface energy coatings, namely silicone or fluoropolymer based coatings that minimize the adhesion strength between fouling organisms and surface. For extended performance life, these coating systems should have controlled and stable surface energy, elastomeric properties, and should adhere well to the substrate.

What is needed is a material that has antimicrobial properties to reduce marine biofouling, thereby decreasing the accumulation and buildup of marine organisms and aiding in their removal. Such a material would preferably lack toxic copper or tin metals, and lower the strength of adhesion between marine fouling organisms and surfaces in contact with a marine environment. The diversity of fouling organisms and environmental conditions worldwide makes the task of developing a coating that resists fouling and/or self-cleans challenging, and novel solutions to the problem are urgently needed.

SUMMARY

The invention provides a polymer that includes a plurality of two-carbon repeating units in a polymer chain, wherein one or more of the two-carbon repeating units of the polymer chain have pyridine-containing substituents; and at least about 10% of the nitrogen atoms of the pyridine-containing substituents are quaternized with $(C_1-C_{30})$alkyl groups or with an alkyl group that contains one or more ethylene glycol groups.

The polymer of the invention can also include one or more polymer chain substituents selected from aryl groups, alkyl groups, and alkoxycarbonyl groups, wherein any alkyl, aryl, or alkoxy is optionally substituted with one or more alkyl, alkoxy, halo, dialkylamino, trifluoromethyl, ethylene glycol, or perfluoroalkyl groups.

The alkyl groups that are used to quaternized the pyridine-containing substituents can be at least partially fluorinated. The ethylene glycol groups used to quaternized the pyridine-containing substituents can have alkyl groups in their chain that are also at least partially fluorinated. For example, at least about 10% of the $(C_1-C_{30})$alkyl groups can be at least partially fluorinated. In another embodiment, at least about 20% of the $(C_1-C_{30})$alkyl groups are at least partially fluorinated. In other embodiments, at least about 50%, or about 80% to about 99% of the $(C_1-C_{30})$alkyl groups can be at least partially fluorinated.

The polymer can have at least about 50% of the nitrogen atoms of the pyridine-containing substituents quaternized with $(C_1-C_{30})$alkyl groups. In polymers with fewer than 100 pyridine groups, the number of quaternized pyridines or partially fluorinated alkyl groups as indicated by any percentage limitation can be rounded up to the nearest integer.

One or more of the partially fluorinated $(C_1-C_{30})$alkyl groups can be, for example, $(C_6-C_{10})$perfluoroalkyl$(C_3-C_{10})$ alkyl groups. A specific example of a $(C_6-C_{10})$perfluoroalkyl-$(C_3-C_{10})$alkyl groups is a 6-perfluorooctyl-1-hexyl group.

The polymer can exhibits antifouling properties. Antifouling properties include antimicrobial and antialgal properties, such as activity against marine algae, algal spores, bacterial cells, diatoms, and protozoa.

The polymer can have a molecular weight of about 5 kDa to about 500 kDa. In some embodiments, the polymer can have a molecular weight of about 10 kDa to about 150 kDa.

The invention also provides an antifouling surface that includes a surface coating comprising a polymer as described herein. The antifouling surface can be prepared by coating a surface with a polymer of the invention. The antifouling surface can also include a base layer of a different polymer, for example, a plexiglass or an elastomeric polymer.

The invention further provides a polymer that includes at least one segment of formula I:

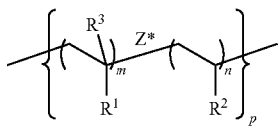

wherein
each R¹ is independently aryl or alkoxycarbonyl;
each R² is independently a pyridine or a pyridine ($C_1$-$C_{10}$) alkyl group, wherein at least 10% of the nitrogen atoms of the pyridine moieties are quaternized with ($C_1$-$C_{30}$)alkyl groups or with an alkyl group that contains one or more ethylene glycol groups;
each R³ is independently hydrogen or methyl;
wherein any alkyl, aryl, or alkoxy is optionally substituted with one or more alkyl, alkoxy, halo, dialkylamino, trifluoromethyl, ethylene glycol, or perfluoroalkyl groups;
each m is about 5 to about 2000;
each n is about 5 to about 2,000;
p is about 5 to about 100; and
the dispersement of each individual m subunit and each individual n subunit on either side of z* is random and each individual m subunit and each individual n subunit occurs interchangeably with any other m or n subunit within the brackets of formula I; or
the dispersement of each individual m subunit and each individual n subunit on either side of z* is that of a block copolymer.

The dispersement of subunits on either side of z* indicates that the polymer can be prepared by either anionic polymerization, free-radical polymerization, or any other technique known to those of skill in the art. The resulting polymer can thus be a random copolymer, terpolymer, etc., or the polymer can be a block polymer with two or more different types of blocks.

In one embodiment, each R¹ can be phenyl or butoxycarbonyl, or a combination thereof. In one specific embodiment, each R¹ is phenyl and the polymer is a block copolymer. In another embodiment, each R¹ is butoxycarbonyl and the polymer is a random copolymer.

In one embodiment, each R² is 4-pyridine. Other pyridine substitutions can also be used, for example, 2-pyridines and 3-pyridines. The pyridine groups can be at least 20% quaternized with partially fluorinated ($C_1$-$C_{30}$)alkyl groups. The pyridine groups can also be at least 20% quaternized with non-fluorinated ($C_1$-$C_{30}$)alkyl groups.

At least about 10% of the ($C_1$-$C_{30}$)alkyl groups are at least partially fluorinated.

The values of m, n, and p can be selected such that the molecular weight of the polymer is about 5 kDa to about 500 kDa, about 10 kDa to about 250 kDa, about 20 kDa to about 150 kDa, or about 40 kDa to about 100 kDa.

The polymers can be employed to prepare an antifouling surface alone, or in combination with a base layer of another polymer, for example, a plexiglass or an elastomeric polymer.

The invention further provides a method of preparing an antimicrobial surface that includes coating at least a portion of a surface with a polymer that has a plurality of two-carbon repeating units in a polymer chain, wherein one or more of the two-carbon repeating units of the polymer chain have nitrogen-containing substituents;
the nitrogen-containing substituents comprise tertiary amines or pyridine groups; and (a) at least about 10% of the nitrogen atoms of the nitrogen-containing substituents are quaternized with ($C_1$-$C_{30}$)alkyl groups; or (b) at least about 10% of the nitrogen atoms of the nitrogen-containing substituents are quaternized with an alkyl group that contains one or more ethylene glycol groups; to provide the antimicrobial surface.

The polymer of the antimicrobial surface can have at least about 10% of the ($C_1$-$C_{30}$)alkyl groups can be at least partially fluorinated. In other embodiments, at least about 50%, at least about 80%, or at least about 90% of the ($C_1$-$C_{30}$)alkyl groups are at least partially fluorinated.

The invention further provides a block copolymer that includes polymerized 4-vinyl pyridine in a first block and styrene in a second block, wherein at least about 10% of the nitrogen atoms of the 4-vinyl pyridine groups are quaternized with ($C_1$-$C_{30}$)alkyl groups, and wherein at least about 10% of the ($C_1$-$C_{30}$)alkyl groups are at least partially fluorinated.

In any polymer of the invention, the terminal groups of the polymer will be determined by the method of polymerization used and the respective initiator and quench used in the preparation process. One skilled in the art will readily understand the variety of terminal groups that can be provided by the initiators and quenching agents. Typical end groups include sec-butyl groups and phenyl groups. Other terminal groups derived from the quenching agent include hydrogen, and various TEMPO and silyl derivatives, for example, a dimethyl (2-perfluorooctyl)ethylsilyl group.

The variables and limitations described for one general or specific embodiment for any polymer described herein can also be applied to other embodiments, for example, other variations of the polymer of the invention and variations of the embodiments provided in the Examples.

1998, 39, 2615-2620). The NEXAFS spectra were obtained at an X-ray incident angle of 55°.

Figure 6:
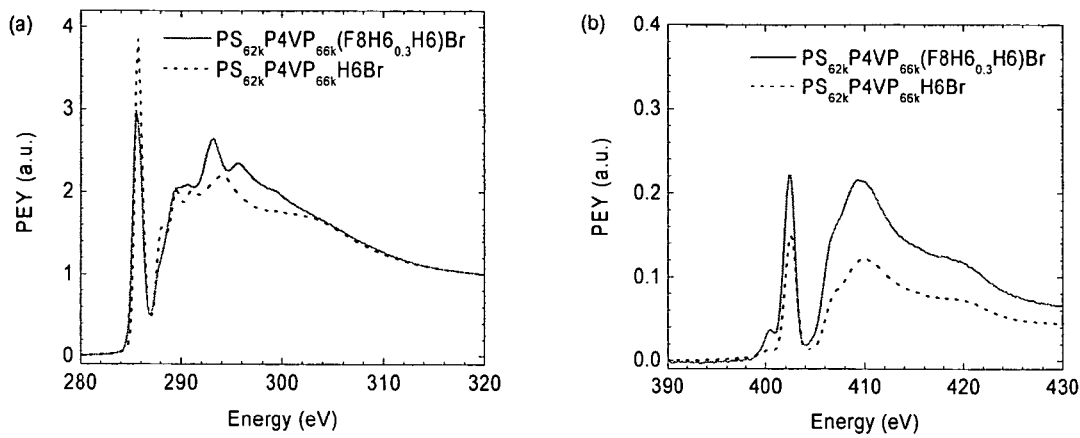

FIG. 6 illustrates C 1 s (left) and N 1 s (right) NEXAFS spectra of spray-coated $PS_{62k}P4VP_{66k}(F8H6_{0.3}H6)Br$ (—) and $PS_{62k}P4VP_{66k}H6Br$ (----) quaternized diblock copolymer surfaces. Spectra were obtained at 55° X-ray incident angle.

Figure 7:
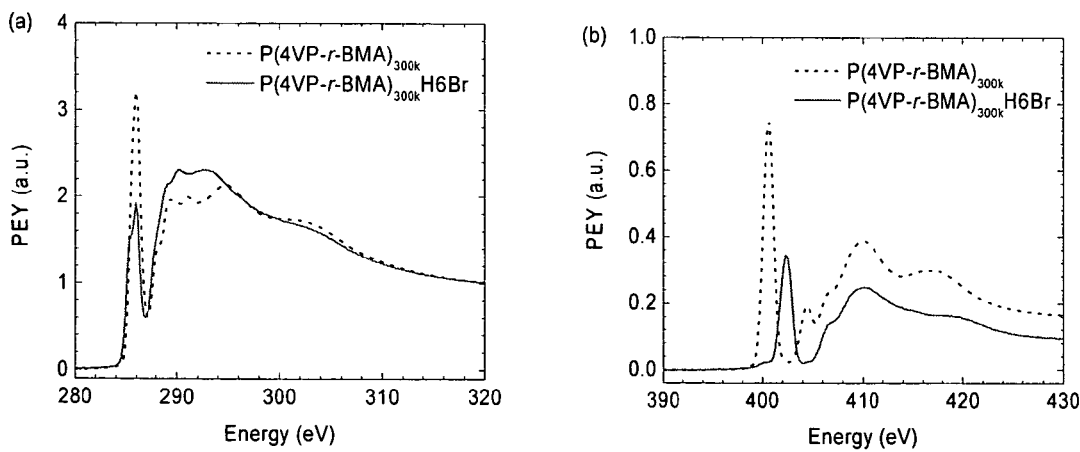

FIG. 7 illustrates C is (left) and N is (right) NEXAFS spectra of poly(4-vinylpyridine-ran-n-butylmethacrylate) surfaces.

Figure 8:
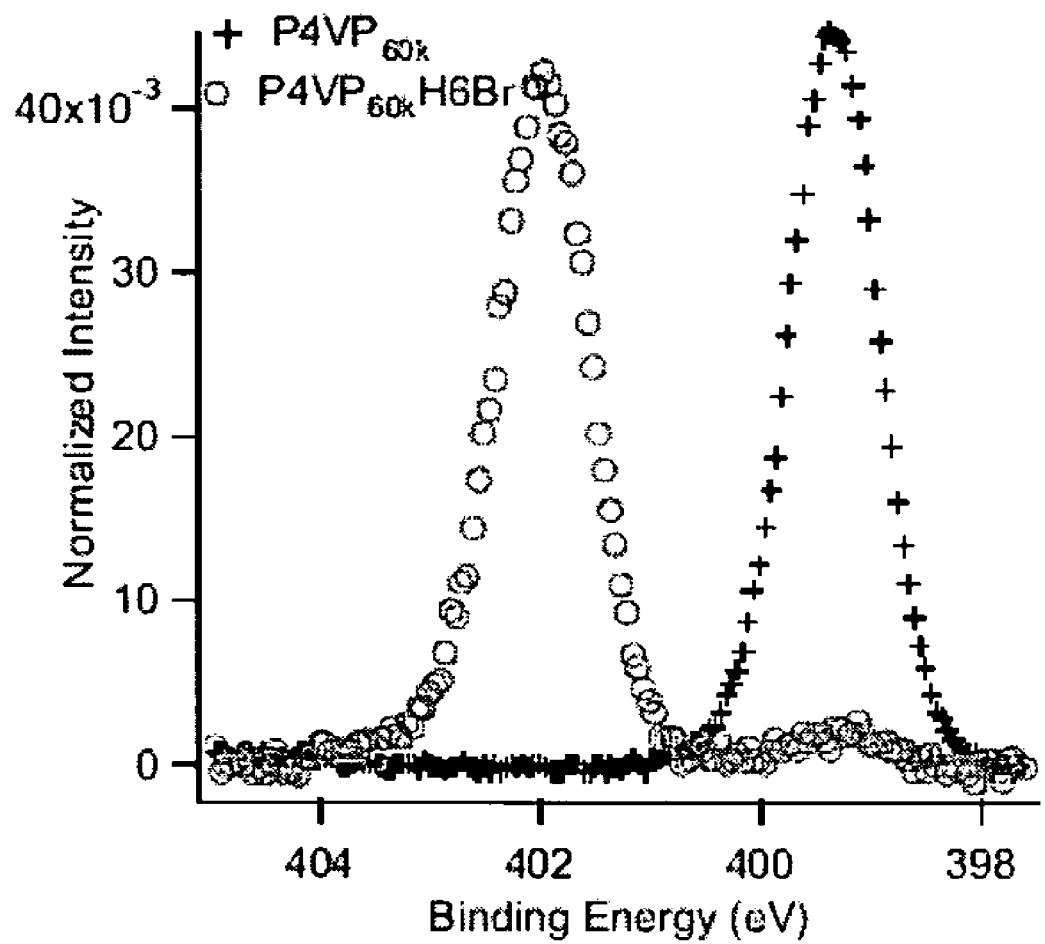

FIG. 8 illustrates N 1 s XPS peaks from the $P4VP_{60k}$ and $P4VP_{60k}H6Br$. Both the peaks are normalized to unit area.

Figure 9:
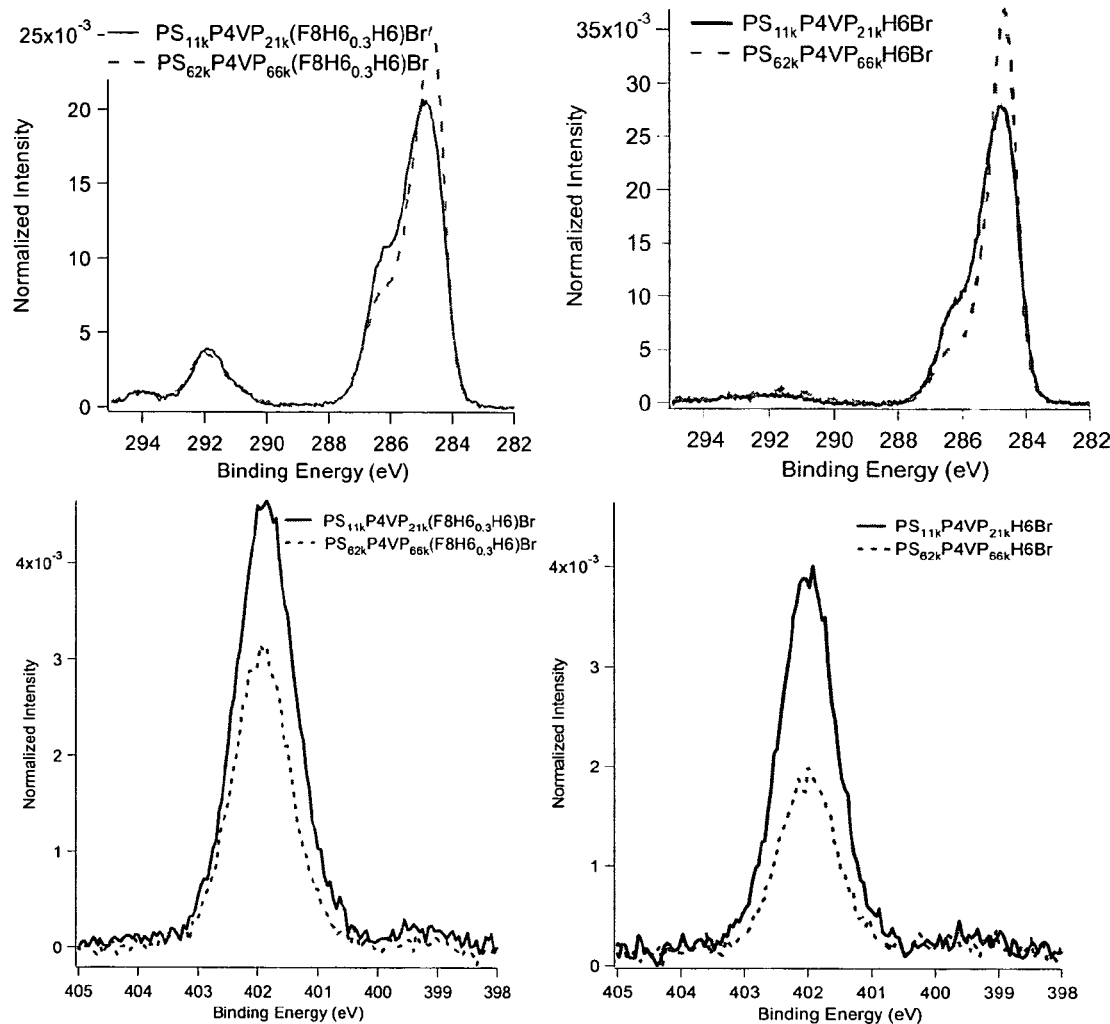

FIG. 9 illustrates C 1 s XPS spectra of spray coated surfaces of (a) fluorinated pyridinium block copolymers, and (b) non-fluorinated pyridinium block copolymers. The corresponding N 1 s spectra are shown in (c) and (d). The carbon peaks were normalized such that the total area under each carbon peak was equal to unity. The nitrogen peaks were normalized so that the area under the N 1 s is proportional to the number of nitrogen atoms, relative to the number of carbon atoms.

Figure 10:
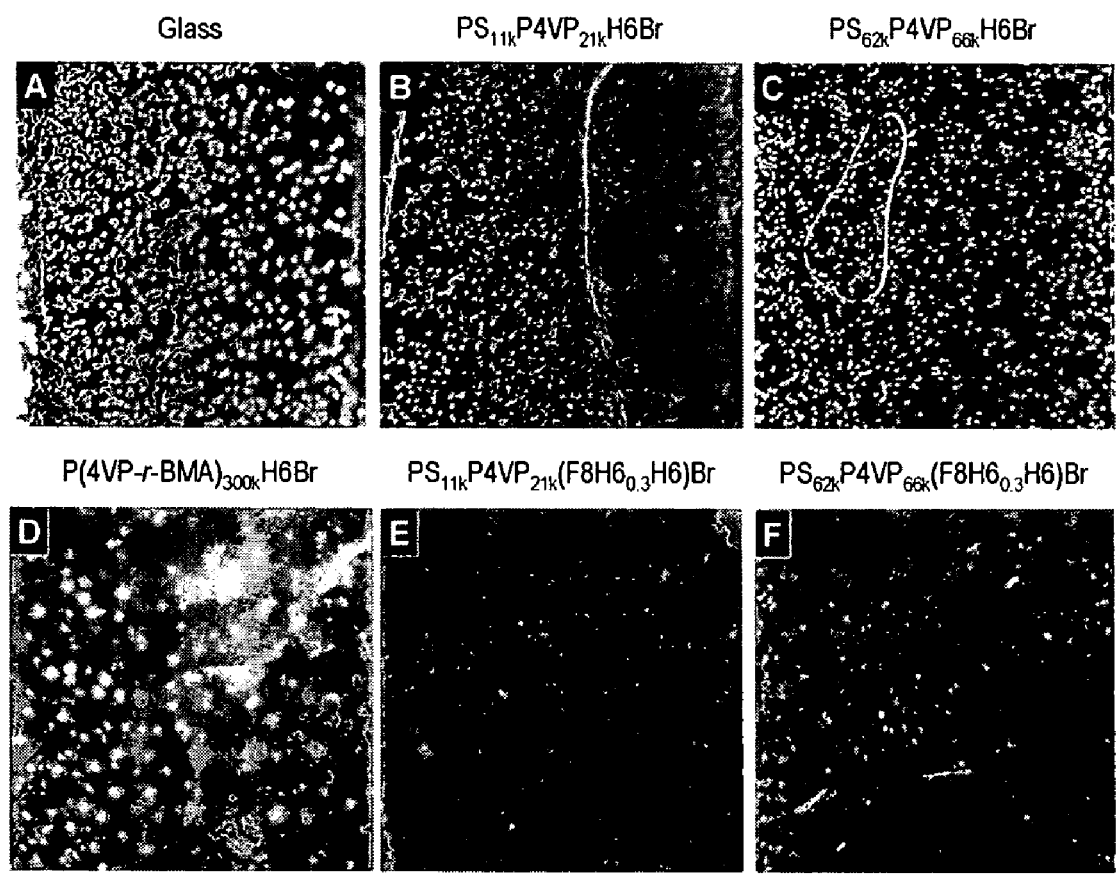

FIG. 10 shows photographs of *S. aureus* colonies on 1 inch×1 inch regions of test surfaces.

Figure 11:
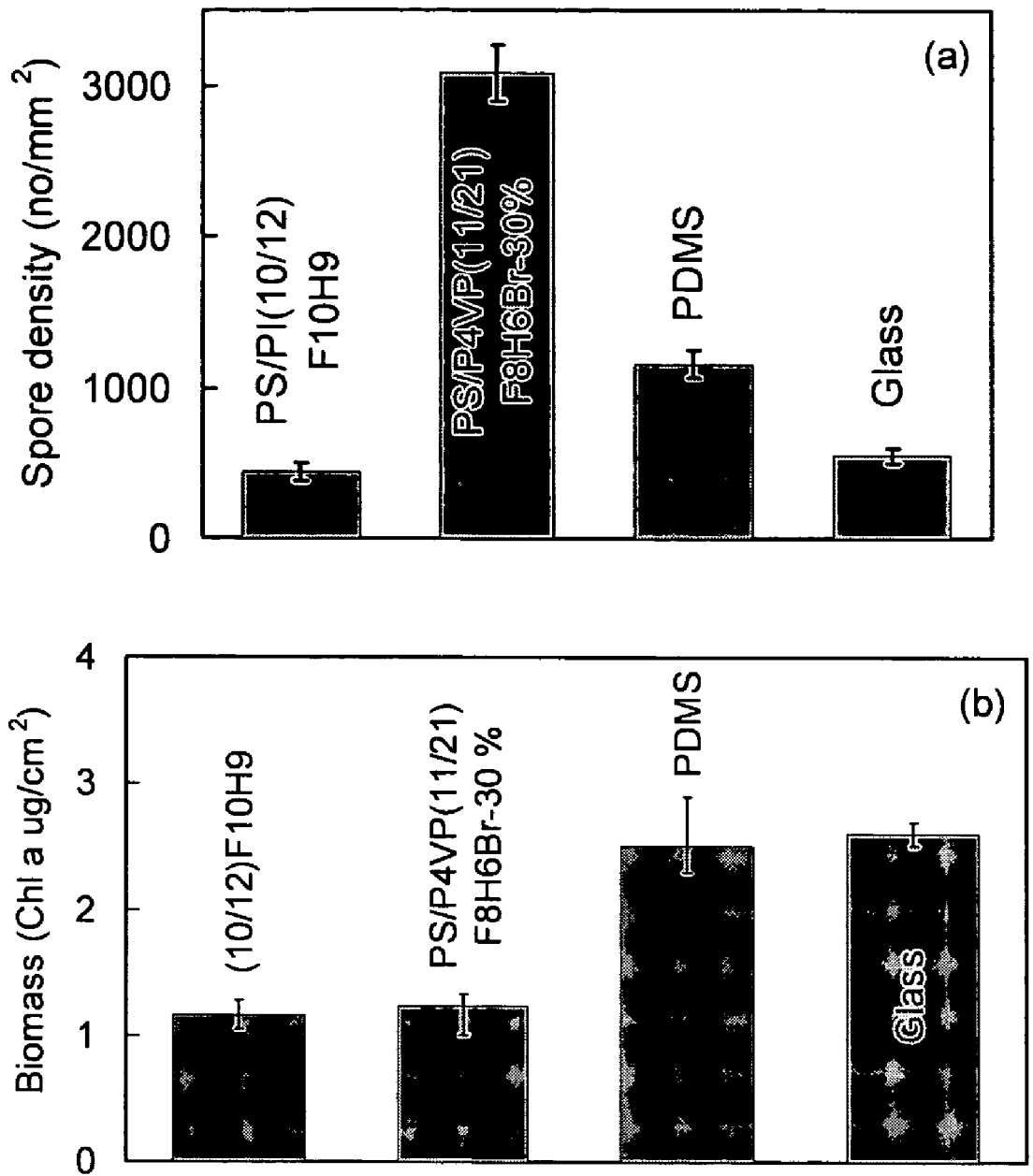

FIG. 11 illustrates (a) settlement of *Ulva* spores and (b) growth of sporelings after 10 days, on PS/PI(10/12)F10H9 and PS/P4VP(11/21)F8H6Br-30% surfaces; PDMS and glass surfaces were used as controls; ■=hydrophobic and ■=hydrophilic.

Figure 12:
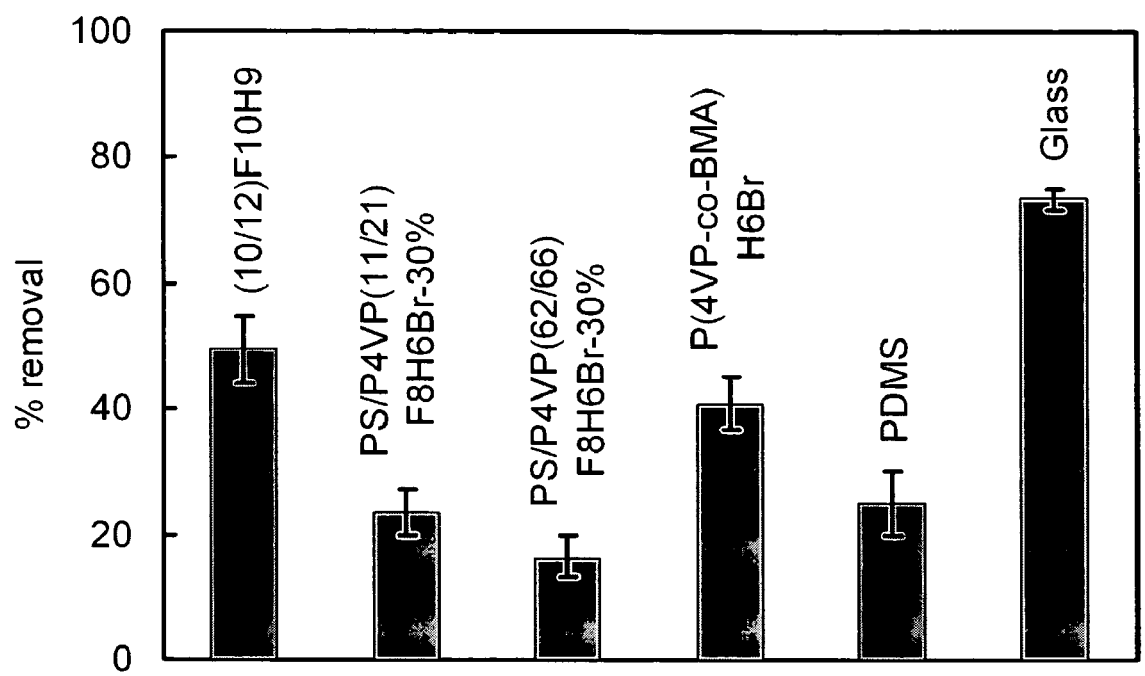

FIG. 12 illustrates detachment of *Navicula* from non-polar block copolymer with semifluorinated side-chains, and polar quaternized 4-VP surfaces with semifluorinated and alkyl side-chains; ■=hydrophobic and ■=hydrophilic.

Figure 13:
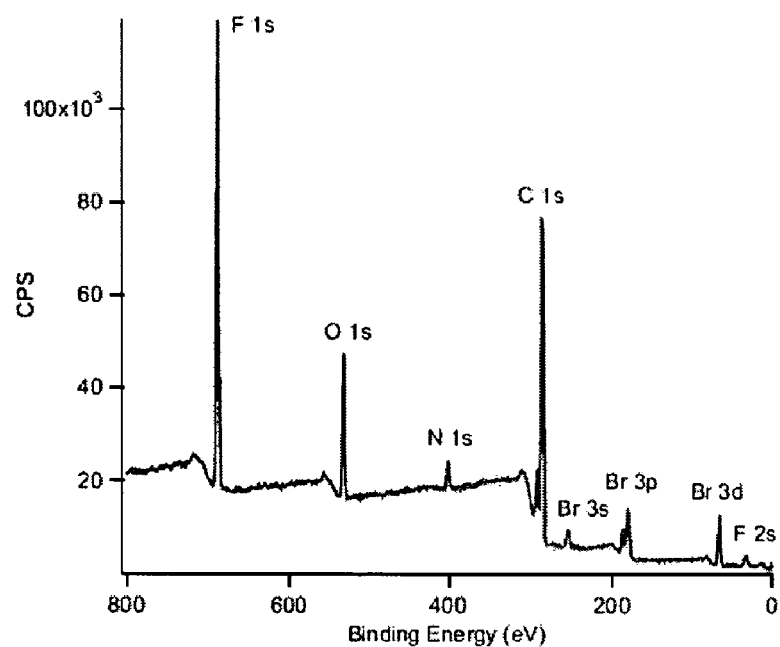
Figure 13:
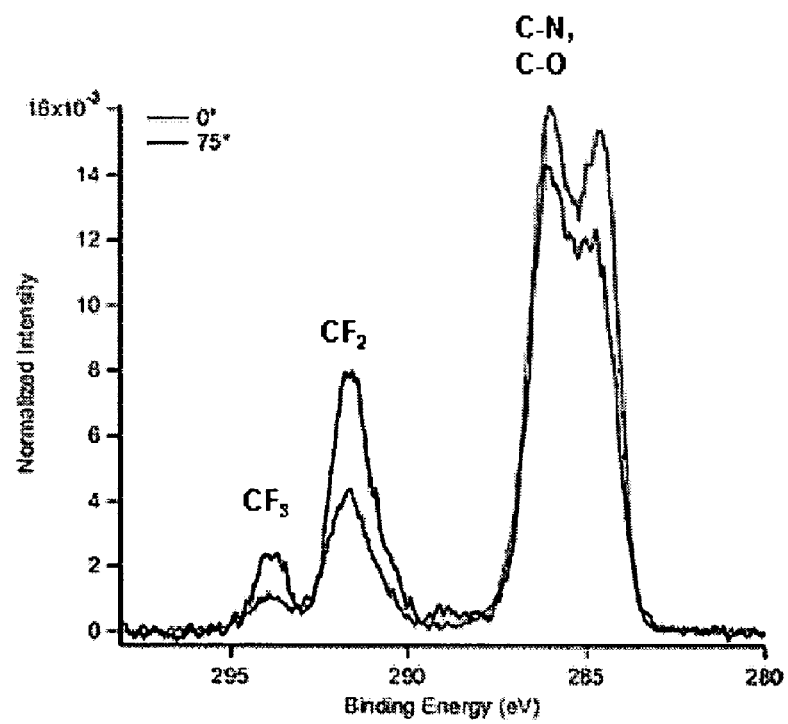

FIG. 13 illustrates XPS survey scan (top) and high resolution C 1 s peaks (bottom) of the pyridinium block copolymer surface prepared by spray-coating onto SEBS covered glass slides.

Figure 14:
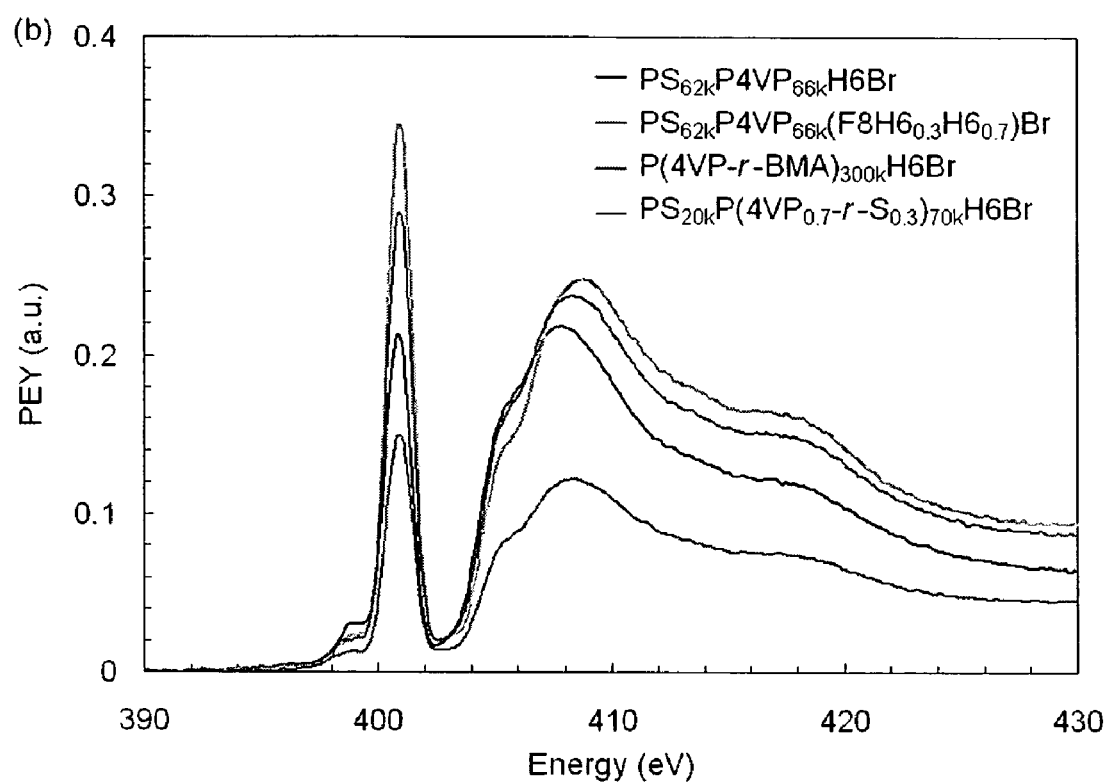

FIG. 14 illustrates (a) C 1 s and (b) N 1 s NEXAFS spectra of quaternized poly(4-vinylpyridine) polymer surfaces.

Figure 15:
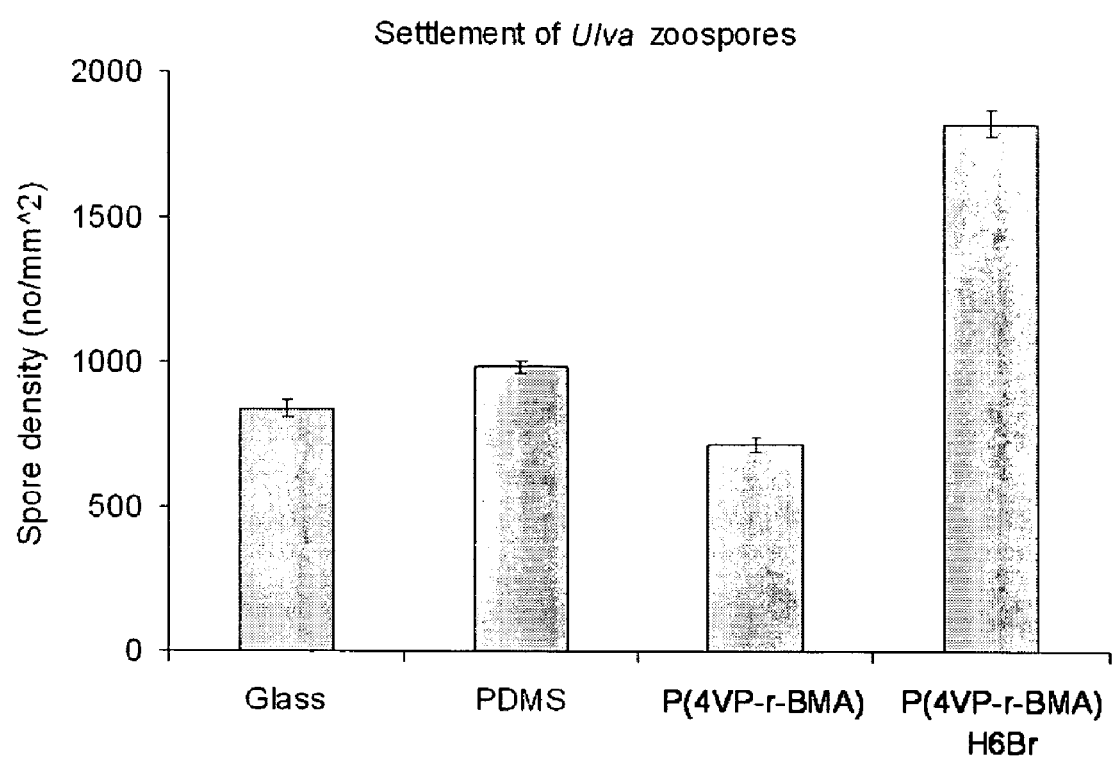

FIG. 15 illustrates the settlement of *Ulva* spores on different surfaces. Each point is a mean from 90 counts on 3 replicate slides. Bars show 95% confidence limits.

Figure 16:
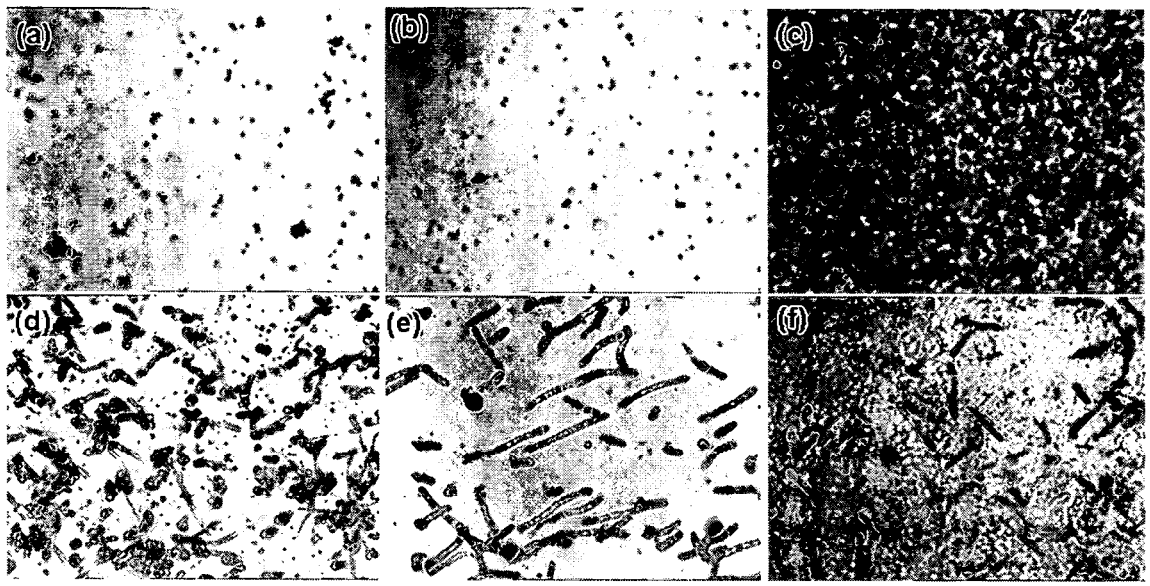

FIG. 16 shows images of settled spores (a, b, and c) and 7 day old sporelings (d, e, and f) on glass (a and d), PDMS (b and e), and $P(4VP-r-BMA)_{300k}H6Br$ (c and f). Image width is approximately 500 μm. The spores used in these experiments were from a different batch than that used to obtain data in FIG. 17.

Figure 17:
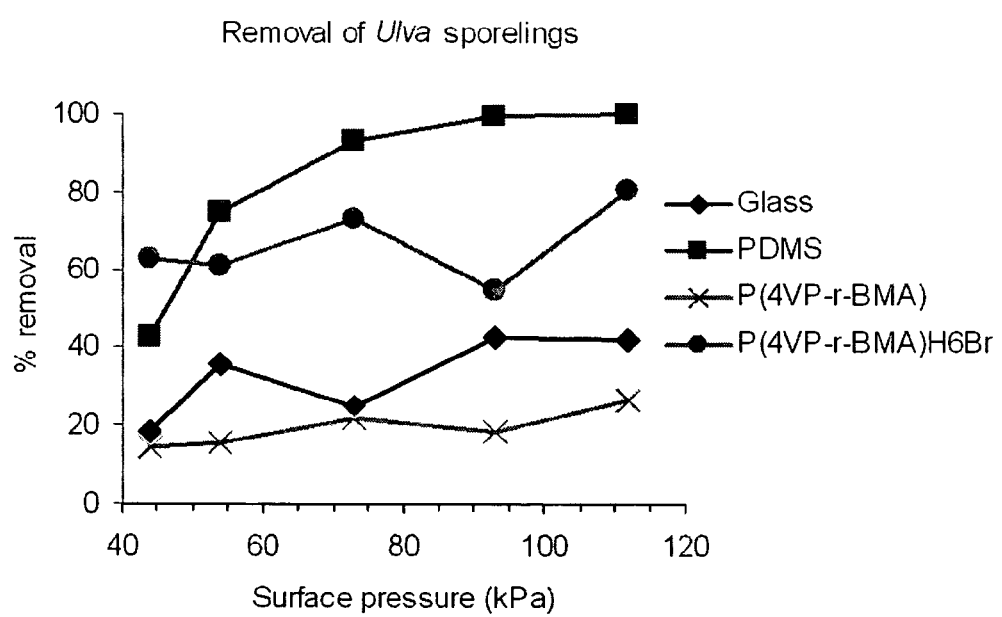

FIG. 17 illustrates detachment of *Ulva* sporelings from different surfaces plotted as % removal after 7 days growth. Coatings were exposed to a range of surface pressures using the water jet.

Figure 18:
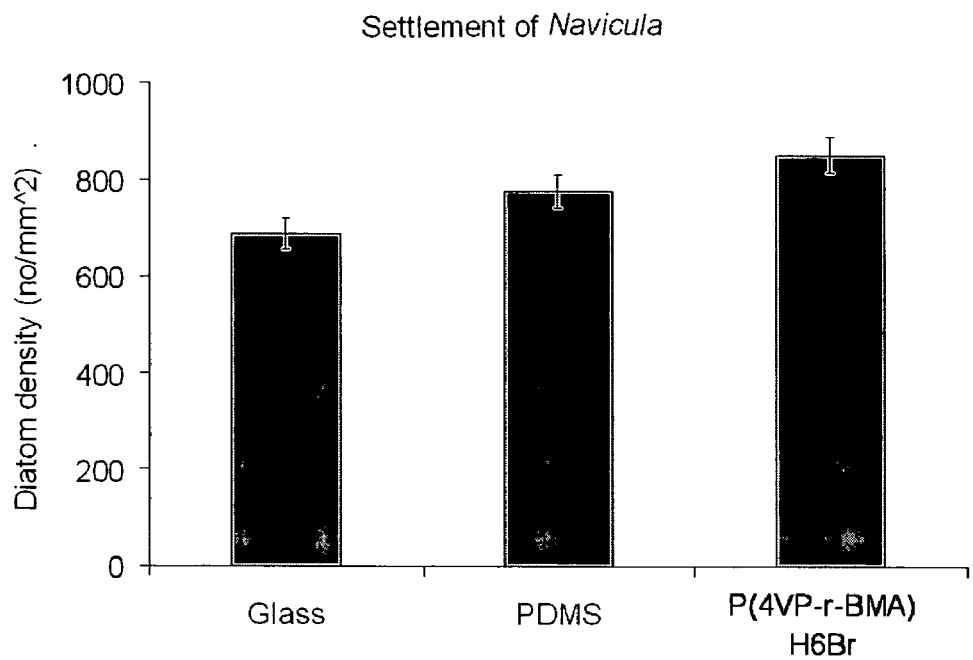

FIG. 18 illustrates settlement of *Navicula* on different surfaces. Each point is the mean from 90 counts on 3 replicate slides. Bars show 95% confidence limits.

Figure 19:
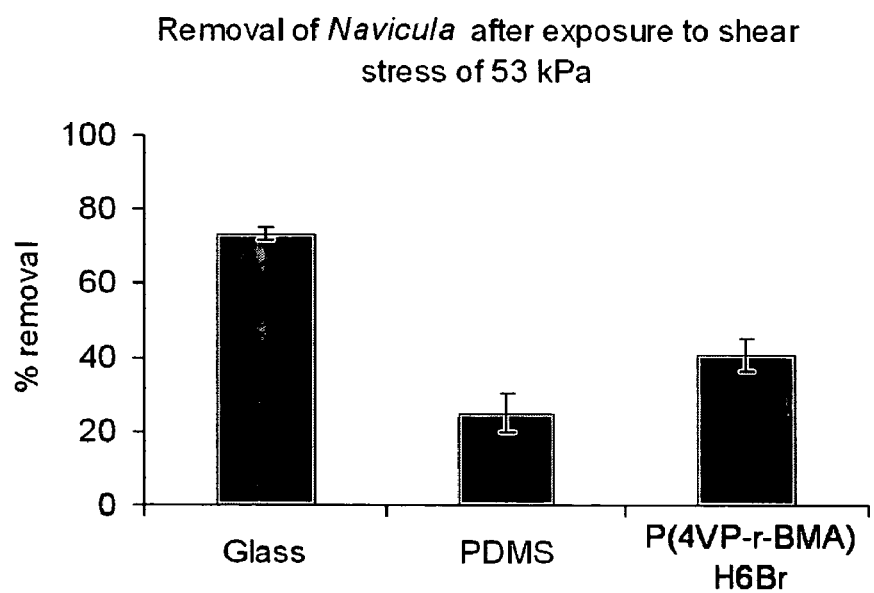

FIG. 19 illustrates detachment of *Navicula* from different surfaces. Each point represents the mean percentage removal from 90 counts from 3 replicate slides. Bars represent 95% confidence limits derived from arcsine transformed data.

Figure 20:
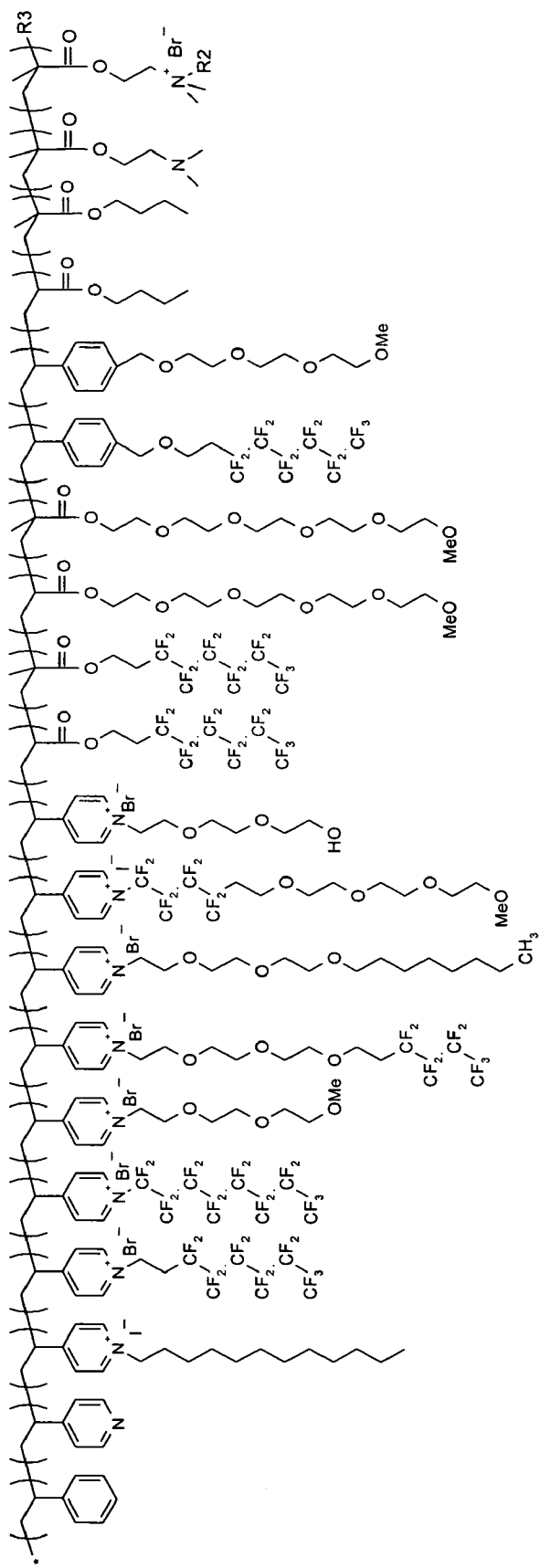

FIG. 20 illustrates various mers of various embodiments of the invention wherein the mers can be selected in any combination in any order to prepare an antifouling polymer. The polymer merely illustrates the variety of mers that can be used in various embodiments and is not an actual polymer that has been prepared.

DETAILED DESCRIPTION

The invention provides polymers that include substituents that contain quaternized nitrogen atoms. The polymers exhibit antimicrobial properties and can be used in antifouling coatings. The quaternized nitrogen groups are tethered to the polymer backbone and can inhibit or prevent the growth of microbes, such as bacterial colonies and/or algal cells, by effecting cell lysis and death. Specific organisms that can be inhibited include *Ulva* (green alga), *Navicula* (diatoms), and *Staphylococcus aureus* bacterium, among others.

The following definitions are used, unless otherwise described. Halo can be fluoro, chloro, bromo, or iodo. Specific values listed below for radicals, substituents, and ranges, are for illustration only; they do not exclude other defined values or other values within defined ranges for the radicals and substituents. The term "about" refers to a value that is greater than or less than the specified value by 5%, 10%, or 25%. The term "about" can also refer to a value that is greater than or less than the specified value by one or two integers.

The phrase "one or more" is readily understood by one of skill in the art, particularly when read in context of its usage. For example, one or more substituents on a phenyl ring refers to one to five, or one to four, for example if the phenyl ring is disubstituted. One or more subunits of a polymer can refer to about 5 to about 50,000, or any increment of about 100 or about 1,000 within that range. In other embodiments, one or more refers to 1 to about 50, 1 to about 30, 1 to about 20, 1 to about 12, 1 to about 10, 1 to about 8, 1 to about 5, 1 to about 3, or 2.

It will be appreciated by those skilled in the art that compounds or polymers of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by synthesis from optically-active starting materials, by using resolution of the racemic form by recrystallization techniques, by chiral synthesis, or by chromatographic separation using a chiral stationary phase). Thus, the compounds and polymers of this invention include all stereochemical isomers arising from the various structural variations of these compounds.

References in the specification to "one embodiment", "an embodiment", "an example embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

"Substituted" is intended to indicate that one or more hydrogens on a group indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, aryloxy, halo, haloalkyl, hydroxy, hydroxyalkyl, aryl, heteroaryl, heterocycle, cycloalkyl, alkanoyl, alkoxycarbonyl, aroyl, acyloxy, aroyloxy, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, ethylene glycol, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. As would be readily understood by one skilled in the art, when a substituent is keto (i.e., =O) or thioxo (i.e., =S), or the like, then two hydrogen atoms on the substituted atom are replaced. The substituent can be separated from the substituted atom by an alkyl chain or ethylene glycol chain, and can be terminated by an alkyl group.

Specific values described for radicals, substituents, and ranges, as well as specific embodiments of the invention described herein, are for illustration only; they do not exclude other defined values or other values within defined ranges, as would be recognized by one skilled in the art.

As used herein, the term "alkyl" refers to a branched, unbranched, or cyclic hydrocarbon having, for example, from 1 to about 30 carbon atoms, and often 1 to about 20, or 1 to about 12 carbon atoms. Examples include, but are not limited to, methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl 4-methyl-2-pentyl, 3-methyl-3-pentyl, 2-methyl-3-pentyl, 2,3-dimethyl-2-butyl, and 3,3-dimethyl-2-butyl, hexyl, octyl, decyl, or dodecyl. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

Alkoxy can be $(C_1-C_{12})$alkoxy, such as, for example, methoxy, ethoxy, propoxy, isopropoxy, butoxy, iso-butoxy, sec-butoxy, pentoxy, 3-pentoxy, hexyloxy, or octyloxy. Any alkyl or alkoxy (including an "alkoxy"-carbonyl) can be optionally unsubstituted or substituted.

The term "aryl" refers to a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like. Aryl can also refer to an unsaturated aromatic carbocyclic group of from 6 to 12 carbon atoms having a single ring (e.g., phenyl) or multiple condensed (fused) rings, wherein at least one ring is aromatic (e.g., naphthyl, dihydrophenanthrenyl, fluorenyl, or anthryl). The aryl can be unsubstituted or substituted.

As used herein, the term "mer" or "mers" refers to a unit of a polymer derived from a particular monomer. For example, a styrene mer refers to a segment of a polymer that was prepared from styrene to form polystyrene, e.g., a phenethyl group wherein the ethyl group is a 1,2-diradical. Accordingly, a mer can refer to a specific unit derived from an unsaturated monomer, thus indicating, for example, a phenethyl diradical within the polymerized chain.

The term "ethoxylated" refers to a group that includes one or more ethoxy (—O—$CH_2$—$CH_2$—) groups, for example, about 2 to about 24 ethoxy groups, or about 3 to about 12 ethoxy groups. An ethoxylated group that has two or more ethoxy or ethylene glycol groups refers to a polyethylene glycol, or PEG group. Ethoxylated or PEG groups can be terminated in an optionally substituted alkyl, for example, a methyl, or they can terminate with hydrogen, e.g., a 2-hydroxyethoxy group.

The terms "semifluorinated" and "at least partially fluorinated" refer to a group, for example an alkyl group, that has at least one hydrogen atom replaced by a fluorine atom. Semifluorinated groups include any carbon chains, or carbon chains that are interrupted by one or more heteroatoms (for example, oxygen), that contain one or more fluorine atoms. Typically the semifluorinated group will have one or more —$CF_2$— groups and can optionally terminate in a —$CF_3$ group. For example, the semifluorinated group can be a group of the formula:

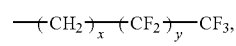

wherein each x is independently about 2 to about 20, and each y is independently 0 to about 20. In other embodiments, x can be about 3 to about 15, and y can be about 5 to about 15. Zonyl surfactants can be considered semifluorinated groups because a portion of the Zonyl surfactant group is a semifluorinated alkyl chain.

Zonyl® surfactants refer to ethoxylated fluoroalkyl chains with terminal alcohol groups. Zonyl® surfactants can be obtained from Dupont (Wilmington, Del.). These surfactants can be attached to appropriately functionalized block copolymers via the hydroxyl group, or via a halo group which has replaced the hydroxyl group. Accordingly, polymers having ethoxylated fluoroalkyl side chains can be prepared using any appropriate Zonyl® surfactant. One example of a suitable Zonyl® surfactant that can be used to prepare ethoxylated fluoroalkyl side chain-containing block copolymers is Zonyl FSO-100 [CAS # 122525-99-9]. Other suitable Zonyl® surfactants include Zonyl FSN, Zonyl FSN-100, and Zonyl FSO.

Ethoxylated fluoroalkyl groups that can be used in various embodiments of the invention include moieties of formula Z:

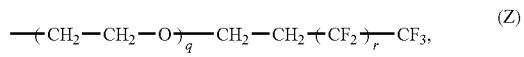

wherein each q is independently 0 to about 25; each r is independently 0 to about 18; and the moiety of formula Z is attached to a polymer chain substituent through an ester, amide, ketone, carbamate, or amine, or is part of a quaternized nitrogen group.

When a nitrogen atom is quaternized, the resulting cation will be accompanied by a corresponding anion. Typically the quaternization is carried out by alkylating a nitrogen atom with an alkyl halide or similar halide, resulting in a halo counterion (anion). Typical halo anions include fluoro, chloro, bromo, and iodo, although bromo and iodo are of particular usefulness. The anions are not, however, limited to halides and polymers with other anions can be prepared by one skilled in the art.

As used herein, "contacting" refers to the act of touching, making contact, or of bringing within immediate proximity.

As used herein, "coating" refers to a manufacturing process or preparation for applying an adherent layer to a workpiece or substrate web. A coating can also be a layer of material that at least partially covers an underlying surface, such as a boat hull, pontoon, or any other surface in need of an antifouling coating.

Methods of Making Compounds, Polymers, and Coatings

Processes for preparing the compounds and surface-active polymers of the invention are provided as further embodiments of the invention. Related compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., *Advanced Organic Chemistry*, $3^{rd}$ Ed., (John Wiley & Sons, New York, 1985), *Comprehensive Organic Synthesis. Selectivity, Strategy & Efficiency in Modern Organic Chemistry*, in 9 Volumes, Barry M. Trost, Ed.-in-Chief (Pergamon Press, New York, 1993 printing).

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be about −100° C. to about 200° C., solvents will be aprotic or protic depending on the conditions required, and reaction times will be about 1 minute to about 10 days. Work-up of standard organic transformation reactions typically consists of quenching any unreacted reagents followed by partition between a water/organic layer system (extraction) and separation of the layer containing the product. Work-up of reactions with polymers typically consists of concentrating the reaction mixture by removing a quantity of solvent, followed by precipitation of the polymer using a solvent or solvent system in which the polymer has low or substantially no solubility, such as, for example, methanol, or a combination of water and methanol.

The polymers of the invention can be synthetically modified, resulting in various substitutions on the mers of the backbone polymer. The mers can be substituted with side groups, such as, for example, semifluorinated (SF), poly(ethylene glycol) (PEG), or ethoxylated fluoroalkyl side groups, or a combination thereof.

General and specific methods for preparing polymers, compositions, and coatings are described in U.S. Patent Application Publication No. US-2006-0083854, which is incorporated herein by reference. The polymers of the invention can be used as protective coatings for surfaces in need of antifouling properties. The coatings can form single layer coatings, bi-layer coatings, or multi-layer coatings. The preparation of bi-layer coatings has been described by Ober et al., U.S. Pat. No. 6,750,296, which is incorporated herein by reference. These techniques can be used to prepare bi-layer coatings that include the polymers described herein.

The invention also provides for a coating composition that includes a polymer that contains a quaternized nitrogen as described herein, in combination with other ingredients. Such other ingredients can include, for example, a polymer, water, one or more solvents, additives, stabilizers, colorants, dispersants, or combinations thereof.

The invention also provides a method of at least partially coating a surface by contacting the surface with a composition containing a polymer that contains a quaternized nitrogen as described herein. The coating procedure can be performed by brushing, immersing, pouring, solvent-casting, spin-coating, or spray-coating to contact the surface with the composition. Accordingly, the invention provides a method of coating or protecting a substrate, for example, a boat hull, from biofouling.

The surface coated by the composition can be a layer of a thermoplastic polymer. The thermoplastic polymer can at least partially covers a boat hull, pontoon, or any other structure in need of such a coating. The average-weight molecular weight of a polystyrene block of the a polymer that contains a quaternized nitrogen as described herein in the composition used to coat the thermoplastic polymer can be within about 20%, or about 10%, or about 5% of the average-weight molecular weight of the polystyrene block or blocks of a polymer comprising the thermoplastic polymer.

A bilayer can be formed and the bilayer can be annealed at a temperature above the glass transition temperature of the polystyrene blocks of the polymers in the bilayer. The coating can result in a top layer of about 30 nm to about 500 µm in thickness. Specifically, the coating can result in a top layer of about 40 nm to about 150 µm in thickness. More specifically, the coating can result in a top layer of about 50 nm to about 25 µm in thickness.

The polymers of the invention can provide a polymer that has an appropriate hydrophilic-lipophilic balance required for cell-membrane disruption effect, thus providing an antifouling coating when used to coat marine surfaces. The polymers can provide a surface chemical composition so that the pyridinium rings (of higher surface energy) are present at sufficient concentrations to latch on to the cell membranes, typically within the outer one to three nm of the surface. The polymers can provide a sufficiently hydrophilic surface to prevent adsorption of extracellular matrices of settling organisms. These extracellular matrices can include proteins, glycoproteins, peptidoglycans, and nucleic acids that the organisms secrete for adhesion.

The amphiphilic nature of the ethoxylated fluoroalkyl chains of the polymers minimize the adhesion strength of marine organisms. Other polymer chain substituents can provide effective screening of the positively charged pyridinium rings so that the surface does not induce microbial settlement. Many embodiments are readily soluble common solvents such as THF, methanol, methylene chloride, chloroform, nitromethane, and nitrobenzene. The polymers have good film forming properties. The polymers can have minimal or no solubility or swelling in water for under-water applications, and minimal or no toxicity to human cells.

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Materials: Styrene (CAS no. 100-42-5, FW 104.15, >99%, Sigma-Aldrich) was stirred over dry di-n-butylmagnesium (received from Sigma-Aldrich as a 1.0 M solution in heptane), and 4-vinylpyridine (CAS no. 100-43-6, FW 105.14, 95%, Aldrich) was stirred over calcium hydride (CAS no. 7789-78-8, 90-95%, Aldrich) for 12 hours and distilled under vacuum after three freeze-thaw-degas cycles.

Tetrahydrofuran (99.9%, Fisher) was distilled from Nal-benzophenone. sec-Butyllithium (s-BuLi, CAS no. 598-30-1, $CH_3CH_2CH(Li)CH_3$, 1.4 M solution in cyclohexane, Aldrich), lithium chloride (CAS no. 7447-41-8, LiCl, FW 42.39, 99.9%, Mallinckrodt), (heptadecafluoro-1,1,2,2-tetrahydrodecyl)-dimethylchlorosilane (CAS no. 74612-30-9, $F(CF_2)_8$ (CH$_2$)$_2$Si(CH$_3$)$_2$Cl, FW 540.72, >95%, Gelest), perfluorooctyl iodide (CAS no. 507-63-1, F(CF$_2$)$_8$I, FW 545.96, >98%, Fluka), 5-hexen-1-ol (CAS no. 821-41-0, HOCH$_2$(CH$_2$)$_3$CH=CH$_2$, FW 100.16, 99%, Aldrich), 2,2'-azobisisobutyronitrile (CAS no. 78-67-1, N≡CC(CH$_3$)$_2$N=NC(CH$_3$)$_2$C≡N, FW 164.21, 98%, Aldrich), tributyltin hydride (CAS no. 688-73-3, (n-Bu)$_3$SnH, FW 291.06, 97%, Aldrich), carbon tetrabromide (CAS no. 558-13-4, CBr$_4$, FW 331.63, 99%, Aldrich), triphenylphosphine (CAS no. 603-35-0, (C$_6$H$_5$)$_3$P, FW 262.29, 99%, Aldrich), and 1-bromohexane (CAS no. 111-25-1, CH$_3$(CH$_2$)$_5$Br, FW 165.07, 98%, Aldrich) were used as received.

Poly(4-vinylpyridine-ran-butyl methacrylate) with a weight-average molecular weight of 300 kDa and 10 wt % of n-butyl methacrylate, anhydrous methylene chloride, N,N-dimethylformamide (DMF) and nitromethane were obtained from Aldrich and used without further purification.

Polystyrene-block-poly(ethylene-co-butylene)-block-polystyrene (SEBS) triblock thermoplastic elastomer (Kraton G1652) was from KRATON Polymers. The solvents, methanol, chloroform, toluene, diethyl ether were purchased from Fisher and used as received.

Example 1

Preparation of Polymers Containing Pyridine or Pyridinium Groups

Synthesis of polystyrene-block-poly(4-vinylpyridine) by anionic polymerization. Polystyrene-block-poly(4-vinylpyridine) were prepared following a literature procedure (Förster et al. *J. Chem. Phys.* 1996, 104, 9956-9970), as illustrated in Scheme 1.

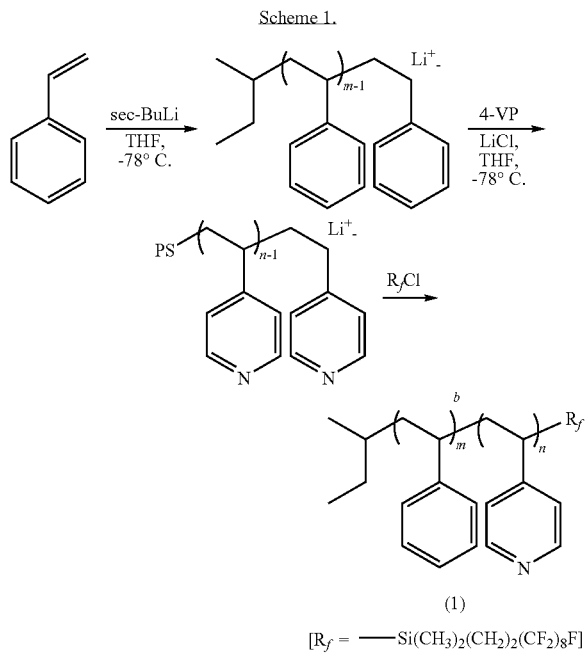

Scheme 1.

[R$_f$ = —Si(CH$_3$)$_2$(CH$_2$)$_2$(CF$_2$)$_8$F]

Polymerization was carried out in tetrahydrofuran at −78° C. using sec-butyllithium initiator. Styrene was stirred with dibutyl magnesium, and 4-vinylpyridine was dried over calcium hydride before distillation under vacuum. Tetrahydrofuran was refluxed over sodium/benzophenone complex and collected in a reaction flask containing lithium chloride (about 5 times the molar amount of sec-BuLi) by distillation.

The initiator (1.4 M solution in cyclohexane) was then injected, followed by the addition of styrene using a cannula. A small amount of the polymer solution was withdrawn from the flask after 45 minutes for molecular weight determination, and was terminated with anhydrous, oxygen-free methanol.

The 4-vinylpyridine monomer was then added to the reaction flask, at which point the color of the solution changed from orange to yellow. After 2 hours of polymerization at −78° C., (heptadecafluoro-1,1,2,2-tetrahydrodecyl)dimethylchlorosilane (10 times molar excess) was injected to terminate the polymer chains. The solution was slowly warmed to about 30° C., at which time a loss of color, signifying termination of the anions, was observed. The final polymer content of the solution was about 5% (w/v).

The monomer conversion, determined from the masses of the monomers added and the mass of the polymer obtained, was close to 100%. Molecular weight of the PS block was determined by gel permeation chromatography (GPC) of the polymer in THF using four Waters Styragel HT columns operating at 40° C., and Waters 490 ultraviolet (λ=254 nm) and Waters 410 refractive index detectors. GPC indicated a narrow distribution with the ratio of weight average molecular weight to the number average molecular weight less than 1.1. The molecular weight of the 4-vinylpyridine block was obtained from the mass of added 4-vinylpyridine and the PS molecular weight.

Two different diblock copolymers were prepared: one with PS and P4VP block molecular weights of 11 kDa and 21 kDa, respectively, designated as PS$_{11k}$P4VP$_{21k}$, and the other with PS and P4VP block molecular weights of 62 kDa and 66 kDa, respectively, designated as PS$_{62k}$P4VP$_{66k}$. The PS-b-P4VP copolymers were quaternized with 6-perfluorooctyl-1-bromohexane (F8H6Br) (4) and 1-bromohexane (H6Br) to obtain block copolymers with semifluorinated side chains (6), as illustrated below in Scheme 4.

Synthesis of semifluorinated alcohol 3. 6-Perfluorooctyl-1-hexanol (CAS no. 129794-54-3, F(CF$_2$)$_8$(CH$_2$)$_6$OH, FW 520.23) was prepared as described in Hopken (Hopken et al. *New Polymeric. Mater.* 1991, 2, 339-356), and as illustrated in Scheme 2 below.

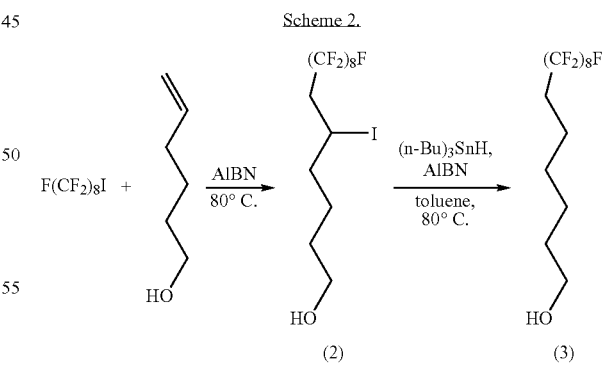

Scheme 2.

Perfluorooctyl iodide (40 g, 73 mmol) and 11 g of 5-hexen-1-ol (109.5 mmol) were heated to 80° C. in a three-neck round-bottom flask fitted with a reflux condenser and purged with nitrogen. About 200 mg (1.22 mmol) of AIBN was added in 4 portions over a period of 6 hours, and the reaction mixture was maintained at 80° C. for a further 6 hours. Excess 5-hexen-1-ol was removed by distillation (bp 56° C. at 11 mmHg). Reduction of iodo-adduct 2 was performed at 80° C.

for about 24 hours by adding 30 mL of anhydrous toluene, 31.9 g (109.5 mmol) of tributyltinhydride, and 0.657 g (4 mmol) of AIBN. The product, which solidified on cooling, was separated by filtration and washed with toluene to remove the tin dimer, (n-Bu)$_3$Sn—Sn(n-Bu)$_3$. The yield was about 60%.

Synthesis of semifluorinated alkyl bromide 4. 6-Perfluorooctyl-1-bromohexane (CAS no. 195247-87-1, F(CF$_2$)$_8$(CH$_2$)$_6$Br, FW 583.12) was synthesized following the procedure of Wang and Ober (*Liquid Crystals* 1999, 26, 637-648; *Macromolecules* 1997, 30, 7560-7567), and as illustrated below in Scheme 3.

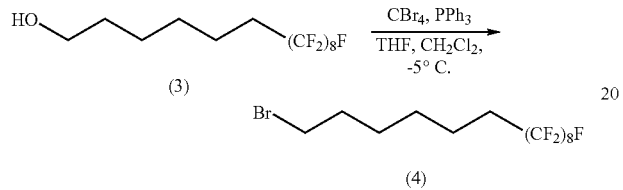

Three grams (5.77 mmol) of 6-perfluorooctyl-1-hexanol and 3 g (9.05 mmol) of CBr$_4$ were dissolved in a mixture of 6 mL of anhydrous THF and 12 mL of anhydrous methylene chloride, and the solution was cooled to −5° C. Triphenylphosphine (2.37 g, 9.05 mmol) of was added in small portions over a period of 15 minutes. After stirring for 1 hour at −5° C. and 6 hours at room temperature, the solvents were evaporated from the reaction mixture under vacuum and about 50 mL diethyl ether was added. An insoluble solid (triphenylphosphine oxide byproduct) was separated by filtration and the filtrate was concentrated to obtain the crude product, which was purified by passing through a short silica gel column with diethyl ether as the elution solvent. The yield was about 85%.

Quaternization of PS-b-P4VP using 1-bromohexane. The PS-b-P4VP polymer was reacted with about 5× moles of 1-bromohexane in anhydrous DMF at 80° C. for about 24 hours under nitrogen. Thus, 1.5 g (7.36 mmol 4-VP) of the PS$_{62k}$P4VP$_{66k}$ diblock copolymer was dissolved in 10 mL of anhydrous DMF and the reaction flask was purged with dry nitrogen for about 15 minutes. Five milliliters of 1-bromohexane (35.6 mmol) was added and the reaction mixture was heated under nitrogen at 80° C. The solution turned dark green within about 2 hours of reaction. After 24 hours, the reaction mixture was cooled to room temperature, and added drop-wise to 200 mL of diethyl ether at 0° C. resulting in a brown precipitate of the polymer (polymer 5 in Scheme 4 below). The solid was dissolved in chloroform, re-precipitated in diethyl ether, and dried under vacuum.

Quaternization of PS-b-P4VP using 6-perfluorooctyl-1-bromohexane.

Quaternization of PS-b-P4VP using 6-perfluorooctyl-1-bromohexane is illustrated below in Scheme 4.

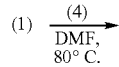

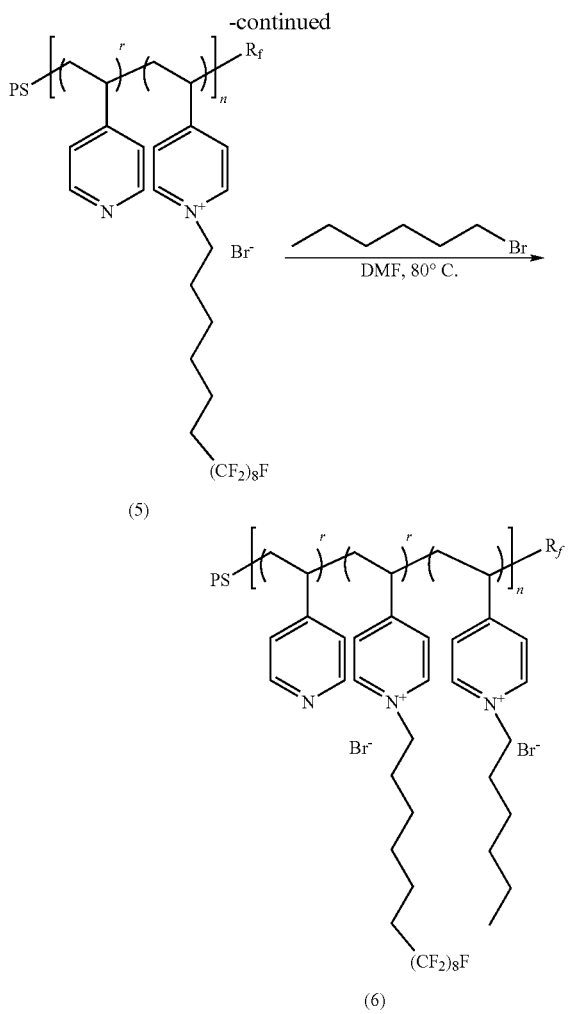

The PS-b-P4VP polymer was reacted with 0.3 equiv of 6-perfluorooctyl-1-bromohexane in anhydrous DMF at 80° C. for about 24 hours under nitrogen. The remaining pyridine groups were further alkylated using an excess of 1-bromohexane at 80° C. for 24 hours. The reactions were carried out sequentially without isolation of the partially quaternized block copolymer 5. Thus, 1 g (4.92 mmol 4-VP) of the PS$_{62k}$P4VP$_{66k}$ diblock copolymer and 0.8630 g (1.48 mmol) of 6-perfluorooctyl-1-bromohexane were dissolved in 10 mL of anhydrous DMF and heated to 80° C. under nitrogen for 24 hours, after which 5 mL (35.6 mmol) of 1-bromohexane was added and the reaction continued for 24 hours at 80° C. After cooling to room temperature the polymer was precipitated in diethyl ether at 0° C. to obtain the partially fluorinated polymer 6 shown in Scheme 4. It was further purified by re-precipitation from a 20% (w/v) solution in chloroform into at least 20 fold volumetric excess of diethyl ether (0° C.) to obtain a fine green precipitate.

Quaternization of P4VP homopolymer and P(4VP-co-BMA) random copolymer using 1-bromohexane. P4VP (2.5 g) with a molecular weight of 60 kDa, was reacted with 4.3 g of 1-bromohexane (10% molar excess) in 25 g of nitromethane at 80° C. for about 2 days. The color of the solution changed from bright green to dark green and finally brown. After cooling to room temperature, the viscous solution was poured into diethyl ether at 0° C. to obtain the quaternized polymer as a brown precipitate. Poly(N-hexyl-4-vinylpyridine-ran-n-butyl methacrylate) random copolymer was similarly prepared by reacting 6 g of P(4VP-co-BMA), with an average molecular weight of 300 kDa, with 8 mL of 1-bromohexane in 60 mL of nitromethane at 80° C. for 2 days, followed by precipitation of the polymer in diethyl ether.

Results and Discussion: The PS-b-P4VP polymers were easily soluble in dimethyl formamide. The use of DMF as a solvent resulted in a high degrees of quaternization within shorter reaction times compared to chloroform, possibly due to higher reaction temperatures that could be used under non-pressurized conditions. Moreover, the $PS_{11k}P4VP_{21k}$ formed a cloudy solution in chloroform, suggesting micelle formation.

The pyridinium block copolymer prepared by reacting 0.3 equiv of 6-perfluorooctyl-1-bromohexane with the $PS_{62k}P4VP_{66k}$ block copolymer, is denoted by $PS_{62k}P4VP_{66k}$(F8H6$_{0.3}$H6)Br. The polymer $PS_{11k}P4VP_{21k}$(F8H6$_{0.3}$H6)Br was similarly prepared by reacting $PS_{11k}P4VP_{21k}$ with 0.3 equivalents of F8H6Br followed by an excess of H6Br. The $PS_{11k}P4VP_{21k}$ and $PS_{62k}P4VP_{66k}$ block copolymers quaternized with 1-bromohexane alone are denoted by $PS_{11k}P4VP_{21k}$H6Br and $PS_{62k}P4VP_{66k}$H6Br, respectively. These were readily soluble in chloroform or chloroform/methanol mixtures to form clear solutions or cloudy micellar dispersions.

All the block copolymers were end-capped with perfluorooctyl groups, however the $PS_{62k}P4VP_{66k}$(F8H6$_{0.3}$H6)Br and $PS_{11k}P4VP_{21k}$(F8H6$_{0.3}$H6)Br was similarly the F8H6Br side chains are referred to herein as "fluorinated", whereas the $PS_{62k}P4VP_{66k}$H6Br and $PS_{11k}P4VP_{21k}$H6Br polymers without semifluorinated side chains will be referred to as "non-fluorinated".

Initial polymer characterization. Infrared spectra of the polymers were acquired using a Mattson 2020 Galaxy Series FTIR spectrometer. Polymer films for the IR spectroscopy were prepared on salt plates (KBr or NaCl) by drying solutions of the polymers in chloroform. $^1$H and $^{19}$F NMR spectra were recorded using Varian Gemini spectrometer. CDCl$_3$ containing 0.05% (v/v) tetramethylsilane was used as the solvent. Differential scanning calorimetry was performed using a TA Instruments Q1000 series Differential Scanning Calorimeter under nitrogen atmosphere. About 5 mg of sample was used with heating and cooling rates of 10° C./minutes.

Example 2

Characterization, Testing, and Evaluation of Polymer Coatings

The role of surface charge density on antibacterial activity has been recognized in some studies. For example, see Tiller et al. *Biotechnol. Bioeng.* 2002, 79, 465-471; and Kügler et al. *Microbiology* 2005, 151, 1341-1348. Bacterial death occurred only above a threshold value of surface charge density. The experiments described herein using surfaces of poly(4-vinylpyridine) block copolymers showed that besides the length of the pyridinium block, it is the number of pyridinium rings in the top few nanometers of the surface that determines the bactericidal activity. P4VP with a molecular weight of around 21 kDa was found to exhibit almost 100% bactericidal effect against *S. aureus*. Moreover, a surface wherein the pyridinium rings were densely covered by the alkyl side groups was found to be less effective than one in which the pyridinium rings were exposed. Near-edge X-ray absorption fine structure (NEXAFS) spectroscopy and X-ray photoelectron spectroscopy (XPS), which can determine the chemical composition within top 2 to 3 nm of a surface, were used in conjunction with contact angle measurements to study the effect of surface chemistry on bactericidal activity.

Preparation of surfaces for antibacterial tests. Surfaces for bacterial assays were prepared on 3 inch×1 inch glass microscope slides. To improve adhesion of the pyridinium polymers to glass, polystyrene-block-poly(ethylene-ran-butylene)-block-polystyrene (Kraton SEBS G1652) was first spin-coated on the glass slides using a 10% (w/v) solution in toluene and annealed in a vacuum oven at 120° C. for 12 hours. Solutions of the quaternized polymers were then sprayed on the SEBS-coated glass slides (heated to 80° C. on a hot-plate) using a Badger Model 250 airbrush (50 psi nitrogen gas pressure). Samples for NEXAFS and XPS analyses were also prepared by spin coating polymer solutions, typically 3 to 5% (w/v) solutions in chloroform, on silicon wafers using a Cee model 100CB spin coater at 2000 rpm (acceleration of 1000 rpm/s) for 30 seconds.

Contact Angle and Surface Roughness. Contact angles were measured using a NRL contact angle goniometer (Ramé-Hart Model 100-00) at room temperature. Dynamic water contact angle measurements were performed by addition and retraction of a drop of water on the surface. Surface roughness was determined using a 3-D interferometric non-contact surface profiler (ADE Phase-Shift MicroAXM-100HR). Root-mean-square (rms) roughness values were determined over regions of 631 μm×849 μm size and averaged over at least 10 measurements.

NEXAFS Spectroscopy. NEXAFS experiments were carried out on the U7A NIST/Dow materials characterization end-station at the National Synchrotron Light Source at Brookhaven National Laboratory. The X-ray beam was elliptically polarized (polarization factor=0.85), with the electric field vector dominantly in the plane of the storage ring. The photon flux was about $1 \times 10^{11}$ photons/s at a typical storage ring current of 500 mA. A spherical grating monochromator was used to obtain monochromatic soft X-rays at an energy resolution of 0.2 eV. C and N K-shell NEXAFS spectra were acquired for incident photon energy in the range 270 eV to 440 eV. A computer controlled goniometer, to which the sample holder was attached, was used to vary the orientation of the sample with respect to the X-ray beam. The partial-electron-yield (PEY) signal was collected using a channeltron electron multiplier with an adjustable entrance grid bias (EGB). All data reported in this Example are for a grid bias of −150 V.

The channeltron PEY detector was positioned at an angle of 45° with respect to the incoming X-ray beam, and in the equatorial plane of the sample chamber. To eliminate the effect of incident beam intensity fluctuations and monochromator absorption features, the PEY signals were normalized by the incident beam intensity obtained from the photo yield of a "dirty" gold grid (Stöhr *J. NEXAFS Spectroscopy*. Springer-Verlag: N.Y., 1996; Chapter 5, p 114). A linear pre-edge baseline was subtracted from the normalized spectra, and the edge jump was arbitrarily set to unity at 320 eV, far above the C K-edge, a procedure that enabled comparison of different NEXAFS spectra for the same number of carbon atoms.

Figure 1:
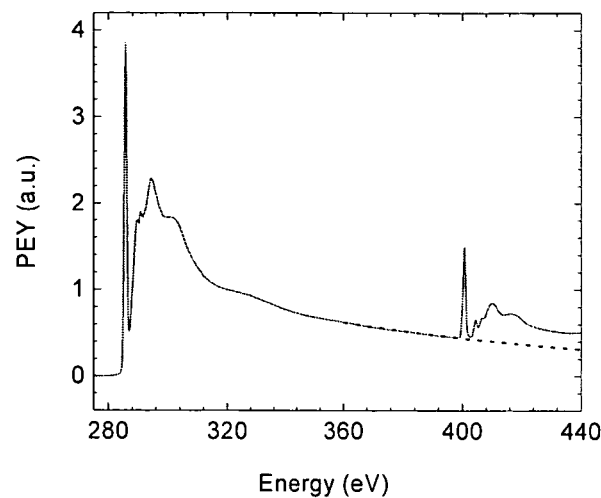
FIG. 1 illustrates C K-edge and N K-edge NEXAFS spectrum of a poly(4-vinylpyridine) surface obtained at an X-ray incident angle of 55° and entrance grid bias at the channeltron electron multiplier of −150 V. The dotted curve shows the exponential background that was subtracted in the N K-edge region.

The N 1 s Auger PEY was determined by subtracting the exponentially decreasing background arising from C atoms in the region between 390 eV and 430 eV, as shown in FIG. 1. Energy calibration was done using a highly oriented pyrolytic graphite (HOPG) reference sample. The HOPG 1 s to π* transition was assigned an energy of 285.5 eV according to the literature value (Rosenberg et al. *Phys. Rev. B* 1986, 33, 4034-4037). The simultaneous measurement of a graphite-coated gold grid allowed the calibration of the photon energy with respect to the HOPG sample. The error in the energy calibration is expected to be within ±0.5 eV. Each measurement was taken on a fresh spot of the sample in order to minimize possible beam damage effects. Charge compensation was carried out by directing low energy electrons from an electron gun onto the sample surface.

X-ray Photoelectron Spectroscopy. X-ray photoelectron spectroscopy (XPS) measurements were performed using a Kratos Axis Ultra Spectrometer (Kratos Analytical, Manchester, UK) with a monochromatic Al Kα X-ray source (1486.6 eV) operating at 225 W under $1.0 \times 10^{-8}$ torr. Charge compensation was carried out by injection of low energy electrons into the magnetic lens of the electron spectrometer. The pass energy of the analyzer was set at 40 eV for high resolution spectra and 80 eV for survey scans, with energy resolutions of 0.05 eV and 1 eV, respectively. The spectra were analyzed using CasaXPS v. 2.3.12Dev4 software. The C—C peak at 285 eV was used as the reference for binding energy calibration.

Antibacterial tests. Viable counts. Five milliliters of Trypticase Soy Broth (TSB; per liter: 17 g casein peptone, 3 g soy meal peptone, 2.5 g D(+)glucose, 5 g NaCl and 2.5 g dipotassium hydrogen phosphate) was inoculated with 100 μL of an overnight culture of S. aureus, and incubated at 37° C. for 4 hours. The cells were centrifuged at 5000 rpm (room temperature) for 1 minute using an Eppendorf model 5415C microcentrifuge, and the pellet was re-suspended in 1 mL sterile filtered water. The suspension of S. aureus (~$10^6$ cells/mL) was sprayed on test surfaces. Sprayed surfaces were dried in air for about 2 minutes and then placed in a sterile petri dish. Molten agar-containing TSB (1.5% w/v of agar) was poured on the slides and allowed to solidify. Plates were incubated at 37° C. overnight (approximately 12 hours). The number of bacterial colonies on the slide surface was counted using a colony counter. Three replicates per polymer were used. Corning glass slides that were not coated with the quaternized polymers were used as controls. Typical density of colonies on the glass controls were 100-150 per $cm^2$ of the surface.

LIVE/DEAD® BacLight™ Bacterial Viability Assay. LIVE/DEAD® Bacterial Viability Kit (BacLight™) was obtained from Molecular Probes Inc. Equal volumes of SYTO® 9 and propidium iodide (received as a solution in anhydrous dimethylsulfoxide) were mixed thoroughly in a microcentrifuge tube. A suspension of S. aureus (~$10^5$ cells/mL) was prepared as described above. The BacLight dye mixture (30 μL) was added to 1 mL of the cell suspension, which was then sprayed on the test surfaces. Immediately after spraying, the test surfaces were covered with glass coverslips and incubated in the dark for 15 minutes. Phase-contrast and fluorescence microscopy were performed, within 30 minutes after spraying, using an Olympus BX61 epifluorescence microscope with a 100× UPlanApo (N.A. 135) objective. The microscope was equipped with filter cubes for viewing SYTO® 9 and propidium iodide fluorescence. Images were acquired using a Cooke SensiCam with a Sony Interline chip and Slidebook software (Intelligent Imaging Inc.). Glass microscope slides were used as controls.

Results and Discussion:

Polymer characterization. In order to interpret the NEXAFS spectra of the block copolymer surfaces, a quaternized homopolymer of 4-vinylpyridine was prepared and used as a reference. P4VP with a molecular weight of 60 kDa was alkylated using 1-bromohexane. Unlike the block copolymers that were not soluble in nitromethane, the quaternization reaction of the P4VP homopolymer could be performed in this solvent. The resulting polymer is denoted by $P4VP_{60k}H6Br$.

A random copolymer of 4-vinylpyridine and n-butyl methacrylate (BMA) with 10 wt. % BMA and a total weight-average molecular weight of 300 kDa was alkylated with 1-bromohexane. The resulting high molecular weight copolymer, denoted by $P(4VP-r-BMA)_{300k}H6Br$, was compared with the quaternized PS-b-P4VP diblock copolymers for antibacterial activity. Surfaces prepared using $P(4VP-r-BMA)_{300k}H6Br$ were found to retain clarity when immersed under water, whereas the $P4VP_{60k}H6Br$ polymer clouded upon water immersion.

Figure 2:
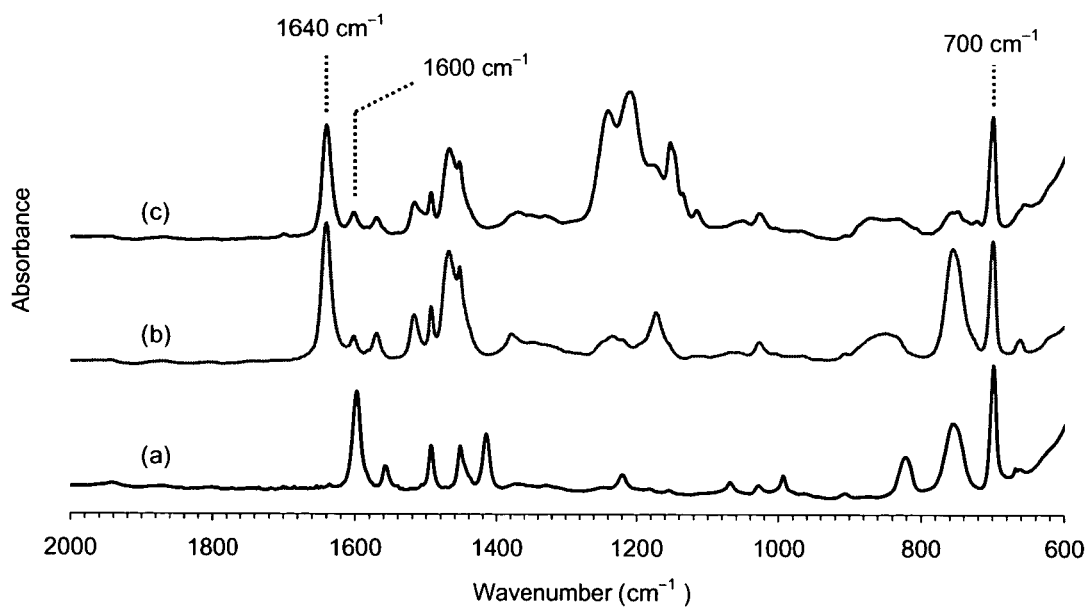
FIG. 2 illustrates IR spectra of (a) $PS_{62k}P4VP_{66k}$; (b) $PS_{62k}P4VP_{66k}$ quaternized with 1-bromohexane; and (c) $PS_{62k}P4VP_{66k}$ reacted with 0.3 equivalents of F8H6Br followed by an excess of H6Br. Preliminary peak assignments: 1640 cm$^{-1}$ C=N$^+$ stretching vibrations; 1200 cm$^{-1}$ to 1300 cm$^{-1}$ C—F stretching vibrations; 700 cm$^{-1}$ styrene C—H bending vibrations.

FIG. 2 shows the IR spectra of the $PS_{62k}P4VP_{66k}$ diblock copolymers. The peak at 700 $cm^{-1}$, arising due to C—H bending vibrations of the styrene phenyl ring, is unique to the PS block and is absent in poly(4-vinylpyridine) homopolymers. The quaternization reaction resulted in an almost complete shift of the peak at about 1600 $cm^{-1}$, corresponding to the C=N stretching vibration of the pyridine ring, to about 1640 $cm^{-1}$. The $PS_{11k}P4VP_{21k}$ polymers showed a similar shift of the peak at 1600 $cm^{-1}$ to 1640 $cm^{-1}$. Thus, the non-fluorinated as well as the fluorinated pyridinium diblock copolymers showed a high degree of quaternization, which was also evident from the XPS spectra of these polymers, as discussed in the NEXAFS Spectroscopy section below. The extent of alkylation of P4VP is usually determined using the relative intensities of the peaks at 1600 and 1640 $cm^{-1}$ (Panov et al. *J. Appl. Spectr.* 1975, 23, 958-962). However, in the case of the quaternized diblock copolymers, the PS block is also expected to show an aromatic C=C stretching resonance at 1600 $cm^{-1}$. Interestingly, as seen in FIG. 2, the 1600 $cm^{-1}$ peak expected for PS is highly suppressed in the quaternized block copolymer, while the aromatic C—H bending resonance of PS at 700 $cm^{-1}$ is quite pronounced.

Figure 3:
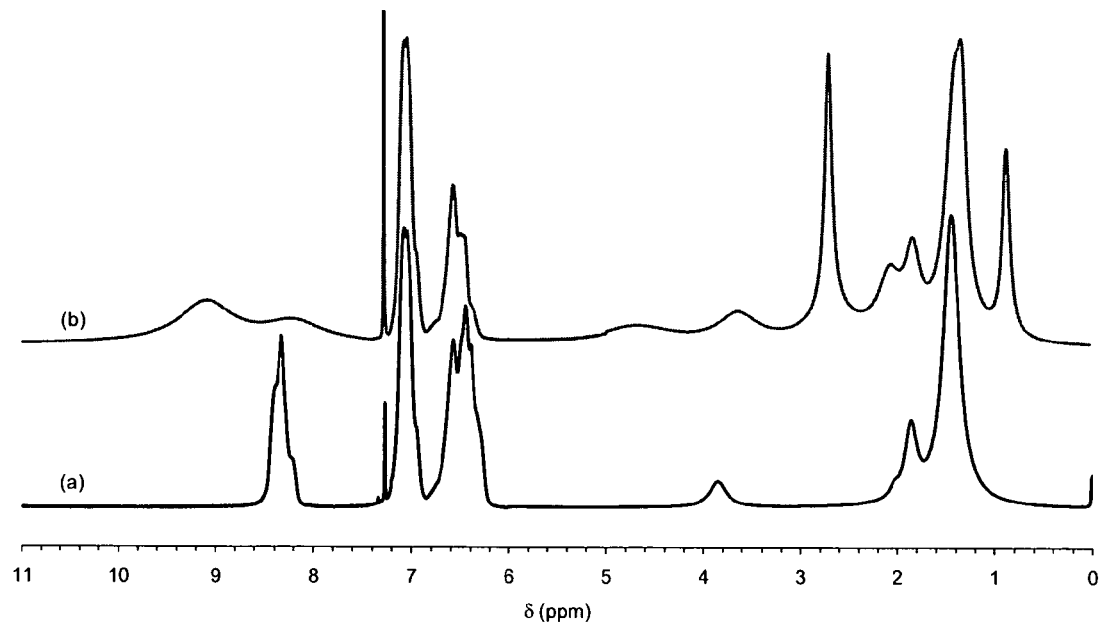
FIG. 3 illustrates 300 MHz $^1$H NMR spectra of (a) $PS_{62k}P4VP_{66k}$ and (b) $PS_{62k}P4VP_{66k}(F8H6_{0.3}H6)Br$ in CDCl$_3$.

The expected polymer composition was further confirmed by $^1H$ and $^{19}F$ NMR spectroscopy. FIG. 3 shows the $^1H$ NMR spectra of the $PS_{62k}P4VP_{66k}$ block copolymer precursor and the $PS_{62k}P4VP_{66k}(F8H6_{0.3}H6)Br$ fluorinated pyridinium polymer. The peak near 8.3 δ in the spectrum of the un-quaternized polymer (FIG. 3a) corresponds to the protons of the pyridine ring ortho to the nitrogen atom. The peaks near 6.4 δ and 7.1 δ result from the meta protons, and the protons of the styrene phenyl rings.

The effect of quaternization is clearly evident in the $^1H$ NMR spectrum of FIG. 3b, where the protons of the pyridine ring now appear at 8.2 δ and 9.1 δ. These $^1H$ nuclei are less shielded due to the positive charge on the carbon atoms of the ring, and thus appear at higher resonance frequencies (or chemical shifts, δ). The positions of the phenyl ring protons remain unchanged. Also seen are the protons of the alkyl side chains, near 0.88 δ and 2.7, δ the former attached to carbon atoms away from the pyridinium ring while the latter attached to carbon atoms closer to the pyridinium ring. The peak near 2.1 δ is likely from the —$CF_2CH_2$— protons of the semifluorinated alkyl side chains (see *Liquid Crystals* 1999, 26, 637-648). The 376.13 MHz $^{19}F$ NMR spectrum of $PS_{62k}P4VP_{66k}(F8H6_{0.3}H6)Br$ showed peaks at −81.4 δ (—$CF_3$), −114.9 δ (—$CF_2CH_2$—), −122.5 δ, −123.4 δ, −124.1 δ and −126.7 δ (—$CF_2CF_3$).

Infrared spectroscopy of the pyridinium homopolymer, $P4VP_{60k}H6Br$, showed a nearly complete shift in the position of the C=N stretching resonance from 1600 $cm^{-1}$ to 1640 $cm^{-1}$ indicating a high degree of alkylation of the P4VP polymer. Using the peak at 1720 $cm^{-1}$ corresponding to C=O stretching vibrations of n-butyl methacrylate as an internal standard, the degree of quaternization in P(4VP-r-BMA)

H6Br was determined by the percent decrease in the absorbance of the C═N stretching peak at 1600 cm$^{-1}$, and was found to be about 94%.

Unlike the semifluorinated alkyl side-chain ionenes (polymers with quaternary nitrogen atoms in the main chains) studied by Wang and Ober (*Macromolecules* 1997, 30, 7560-7567), or the 4-vinylpyridine polymers quaternized with ω-alkylphenylbenzoate derivatives studied by Masson et al. (*Macromol. Chem. Phys.* 1999, 200, 616-620), the pyridinium block copolymers did not show strong thermal transitions by DSC, possibly because of the relatively low density of the semifluorinated alkyl groups along the polymer backbone.

Preparation of test surfaces. The coating formulations are given in Table 1. Glass microscope slides, which were spin-coated with a layer of SEBS, were used as substrates. The SEBS film results in an elastomeric surface in which the cylindrical domains formed by the PS end-blocks (~7.5 kDa mol. wt.) act as physical crosslinks in a matrix of the poly (ethylene-ran-butylene) central block (~35 kDa mol. wt.). About 3 mg of the pyridinium polymer was used per cm$^2$ of the surface. The spray-coated surfaces were dried in a vacuum oven at 60° C. for 24 hours. The properties of the surfaces, characterized by contact angle measurements and NEXAFS spectroscopy, were found to be fairly sensitive to the coating formulation and processing.

TABLE 1

Solutions used to prepared surfaces for antibacterial tests.

| Polymer | Formulation | Solution appearance |
|---|---|---|
| PS$_{11k}$P4VP$_{21k}$H6Br* | 1.5% (w/v)$^§$ in 1:1 (v/v) chloroform-methanol blend | Clear, pale yellow |
| PS$_{62k}$P4VP$_{66k}$H6Br* | 1.5% (w/v) in chloroform | Cloudy |
| PS$_{11k}$P4VP$_{21k}$(F8H6$_{0.3}$H6)Br$^†$ | 1.5% (w/v) in 1:1 (v/v) chloroform-methanol blend | Clear, dark green |
| PS$_{62k}$P4VP$_{66k}$(F8H6$_{0.3}$H6)Br$^†$ | 1.5% (w/v) in chloroform | Clear, dark green |
| P(4VP-r-BMA)$_{300k}$H6Br* | 1.5% (w/v) in chloroform | Clear, pale yellow |

*P4VP precursors quaternized using a molar excess of 1-bromohexane alone.
$^†$P4VP precursors reacted with 0.3 equivalents of 6-perfluorooctyl-1-bromohexane followed by reactions with an excess of 1-bromohexane.
$^§$1.5% (w/v) = 0.015 g/mL.

Water Contact Angle Measurements. Table 2 lists the advancing and receding water contact angles (CA), denoted by $θ_{w,adv}$ and $θ_{w,rec}$, respectively, on the spray-coated surfaces used in the antibacterial tests. The variation in the measured values was within ±2° and the values reported are averages of at least 5 measurements. The rms roughness values, determined by optical interferometry, were close to 1 μm—about 0.6 μm for PS$_{11k}$P4VP$_{21k}$(F8H6$_{0.3}$H6)Br, 0.9 μm for PS$_{62k}$P4VP$_{66k}$(F8H6$_{0.3}$H6)Br, and 1.1 μm for P(4VP-r-BMA)H6Br. An un-quaternized PS-b-P4VP copolymer, spin-coated on a silicon wafer and annealed in vacuum at 150° C. for 15 h had $θ_{w,adv}$ and $θ_{w,rec}$ values of 95° and 69°, respectively, similar to those for a polystyrene surface.

Thus, it can be inferred that the surface at equilibrium is covered by the lower surface-energy PS block at equilibrium, as expected (surface energy of PS is about 39.3 mJ/m$^2$ and that of P4VP is 68.2 mJ/m$^2$; see Jiang et al. *Polymer* 1998, 39, 2615-2620). However, the quaternized block copolymer surfaces had lower contact angles (cf. Table 2), indicating the presence of the pyridinium block at the surface. Interestingly, the receding contact angles were lower for the PS$_{11k}$P4VP$_{21k}$(F8H6$_{0.3}$H6)Br and PS$_{62k}$P4VP$_{66k}$(F8H6$_{0.3}$H6)Br surfaces with hydrophobic semifluorinated side groups, than the non-fluorinated PS$_{11k}$P4VP$_{21k}$H6Br and PS$_{62k}$P4VP$_{66k}$H6Br surfaces. One may infer that, in contact with water, the surface-concentration of the hydrophilic pyridinium rings is higher in surfaces with a mixture of F8H6 and H6 alkyl groups. Moreover, the large contact angle hysteresis indicates that these mixed surfaces are mobile, that is, the surfaces can reconstruct to become hydrophilic in the presence of water.

TABLE 2

Advancing and receding water contact angles on spray-coated surfaces.

| | Water CA | |
|---|---|---|
| Surface | $θ_{w,adv}$ | $θ_{w,rec}$ |
| PS$_{11k}$P4VP$_{21k}$H6Br | 73° | 16° |
| PS$_{11k}$P4VP$_{21k}$(F8H6$_{0.3}$H6)Br | 63° | 8° |
| PS$_{62k}$P4VP$_{66k}$H6Br | 55° | 16° |
| PS$_{62k}$P4VP$_{66k}$(F8H6$_{0.3}$H6)Br | 56° | 7° |
| P(4VP-r-BMA)$_{300k}$H6Br | 99° | 10° |

Quaternization of the 4-vinylpyridine polymer did not always result in lowering of the contact angles. A spray-coated surface of poly(4-vinylpyridine-ran-n-butyl methacrylate), annealed at 60° C. for 24 hours, had advancing and receding water contact angles of 72° and 20°, respectively. However, the corresponding quaternized polymer, P(4VP-r-BMA)$_{300k}$H6Br, had $θ_{w,adv}$ and $θ_{w,rec}$ values of 99° and 10°, respectively (cf. Table 2). The higher advancing water contact angle is attributed to a layer of hydrophobic n-hexyl chains covering the pyridinium rings. The lower surface energy —CH$_3$ (~24 mJ/m$^2$) and —CH$_2$— (~31 mJ/m$^2$) groups of the alkyl side chains will be preferentially present at the air-polymer interface, covering the higher energy pyridinium groups (see Pittman, A. G. In *Fluropolymers*, High Polymers Series XXV; Wall, L. A., Ed;. Wiley-Interscience: New York, 1972. p 419-449).

NEXAFS Spectroscopy. NEXAFS spectroscopy allows the determination of the relative numbers of carbon and nitrogen atoms, and also the orientation of bonds in the surface region. The size of the edge jump is proportional to the number of absorbing atoms (C or N), and thus varies with surface concentration (see Stöhr J. *NEXAFS Spectroscopy*. Springer-Verlag: New York, 1996; Chapter 7, p 211). The edge jump is given by the difference of the electron yield about 30 eV above the ionization threshold (320 eV in C 1 s NEXAFS spectra and 430 eV in N 1 s spectra) and the electron yield just below the first resonance. As discussed above, the latter is approximately 0 for both C 1 s and N 1 s spectra, and the C 1 s edge jump has been set to unity.

The NEXAFS spectra reported here were normalized such that the carbon edge jump was the same (=1) for all the surfaces. Hence, the magnitude of the nitrogen edge jump is proportional to the surface concentration of nitrogen atoms relative to carbon. Moreover, a comparison of the intensity of the C 1 s→π* peak (near 285.7 eV for P4VP), is another indication of the presence or absence of pyridinium groups at the surface. Using NEXAFS spectroscopy, a comparison of the surface pyridinium concentrations can be made in a dry state, which the bacterial cells are likely to encounter when they initially contact the surface. Spectrophotometric titration of surface pyridinium groups, involving immersion of the surfaces in aqueous solution of fluorescein dye, has been described by Tiller et al. (*Proc. Natl. Acad. Sci. U.S.A.* 2001, 98, 5981-5985).

Figure 4:
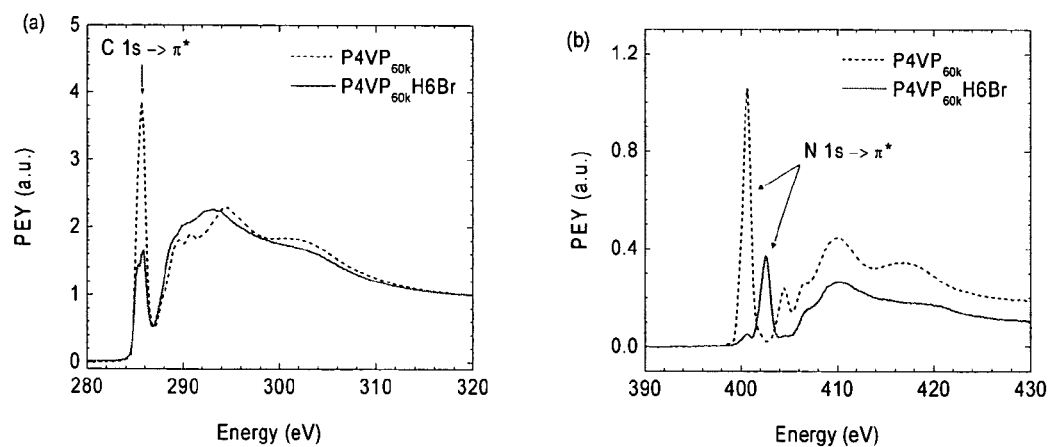
FIG. 4 illustrates C 1 s (a) and N 1 s (b) NEXAFS spectra of surfaces prepared by spin-coating poly(4-vinylpyridine) and poly(N-hexyl pyridinium bromide) from chloroform solutions on silicon wafers; P4VP molecular weight was 60 kDa. The surfaces were annealed for 12 hours in a vacuum oven at 120° C. The spectra were obtained at an X-ray incident angle of 55° and the channeltron entrance grid bias of −150 V.

N-hexylpyridinium surfaces. FIG. 4 shows the C 1 s and N 1 s NEXAFS spectra of surfaces prepared using P4VP$_{60k}$H6Br polymer as well as the P4VP$_{60k}$ precursor. The asymmetry in the shape of the C 1 s→π* peak is attributed to a 1s core level shift arising from differences in the partial charges on the carbon atoms at ortho and meta positions. The ortho atoms that are bonded directly to the nitrogen are more positive than the meta atoms which are further away from the nitrogen (see Kolczewski et al. *J. Chem. Phys.* 2001, 115, 6426-6437). Similarly, the partial charge on the nitrogen atom will be higher than those on the carbon atoms of the ring. Hence, the difference in the resonance energies for the 1 s→π* transition before and after quaternization, is much more pronounced in the N 1 s spectra than in the C 1 s spectra (see Ito et al. *J. Am. Chem. Soc.* 1997, 119, 6336-6344).

Quaternization had a strong effect on the position of the N 1 s→π* resonance, which shifted to a higher energy by about 2 eV (from 400.7 eV for the un-quaternized P4VP$_{60k}$ polymer, to 402.7 eV for the quaternized P4VP$_{60k}$H6Br polymer). Similar shifts were observed in the XPS nitrogen signals of quaternized polymers discussed above and have been reported for P4VP and protonated P4VP by Fujii et al (*J. Am. Chem. Soc.* 2005, 127, 16808-16809).

In FIG. 4, it is seen that the intensity of C 1 s→π*$_{C=C, C=N}$ peak is notably lower for the quaternized surface. The N 1 s→π* resonance for this surface (FIG. 4b) is also lower in intensity compared to the P4VP$_{60k}$ surface. The observed decrease is, in most part, due to the decrease in the transition probability (the number of electrons excited per unit time from the 1 s shell) after quaternization; and also in the case of the N 1 s resonances due to the fact that the nitrogen to carbon atomic ratio in the polymer decreases from 1/7 to 1/13 after quaternization.

If the surface composition is uniform (same as that in the bulk), the relative intensities of the N 1 s→π* peaks at 400.7 eV in the NEXAFS spectra of the un-quaternized and quaternized polymers is an indication of the degree of quaternization. The nitrogen edge jumps of the spectra in FIG. 4b were normalized to the same value so that the comparison was made for the same number of nitrogen atoms in both the surfaces. From the decrease in the intensity of the π* resonance at 400.7 eV in the normalized spectra, it was inferred that more than 90% of the pyridine groups have undergone the quaternization reaction.

The degree of quaternization estimated using this procedure will differ from that obtained by more conventional methods (such as IR or elemental analysis) if the low surface-energy alkyl groups in the quaternized polymer form a thin layer at the surface covering the higher surface energy pyridinium rings. The maximum thickness of this layer can be estimated to be about 7.7 Å, corresponding to a fully stretched n-hexyl chain attached to the pyridinium nitrogen. In such a case, the degree of quaternization obtained from the NEXAFS spectra can be a slight over-estimate.

Figure 5:
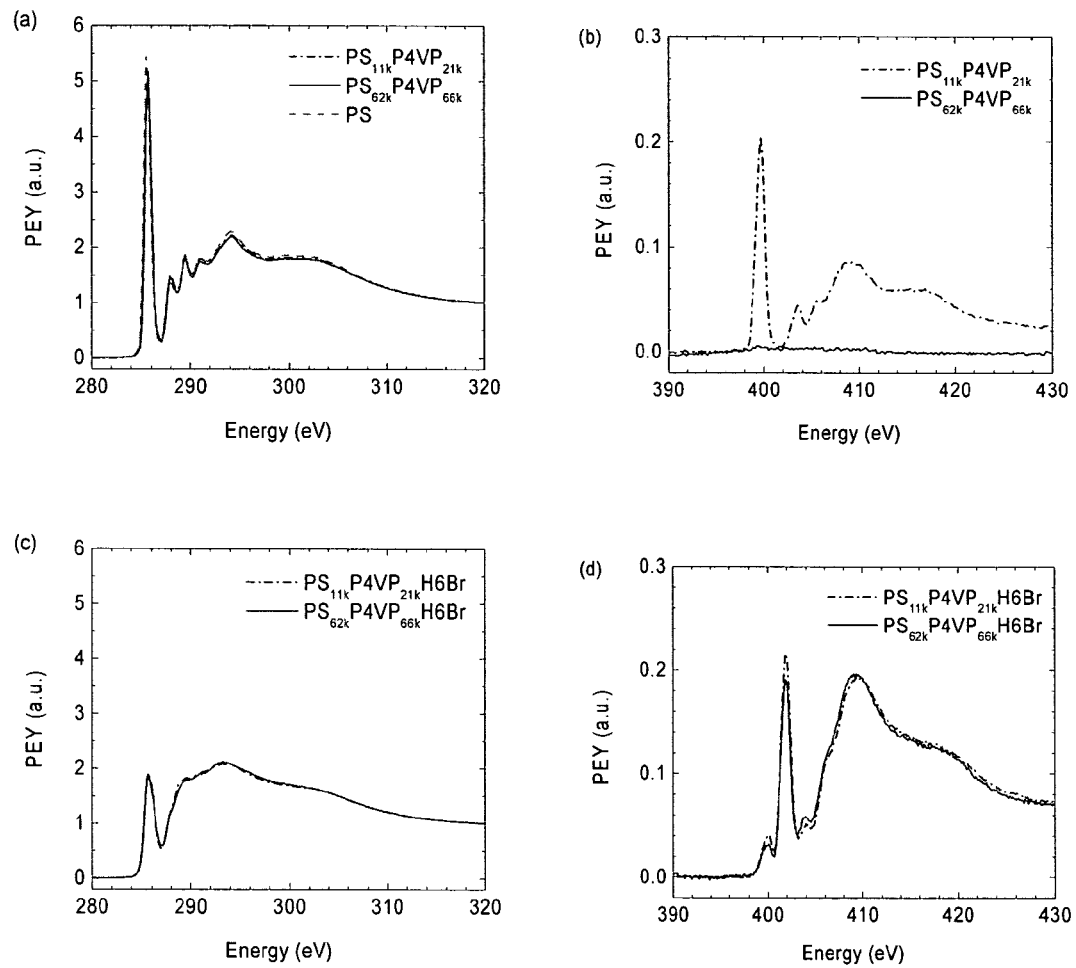
FIG. 5 illustrates C 1 s (left) and N 1 s (right) NEXAFS spectra of PS-b-P4VP copolymers before (a and b) and after (c and d) quaternization with 1-bromohexane. The surfaces were prepared by spin coating 5% (w/v) solutions of the block copolymers in chloroform on silicon wafers and annealing at 150° C., above the $T_g$ of the two blocks, for 12 hours in vacuum. Glass transition temperatures ($T_g$) of PS and P4VP are about 100° C. and 142° C., respectively (see *Polymer*

Rather different results were obtained from the polystyrene-block-poly-(4-vinylpyridine) surfaces. Quaternization of the PS-b-P4VP polymer resulted in an increase in the intensity of the N 1 s resonances in the NEXAFS spectra. The C 1 s NEXAFS spectra of the PS$_{11k}$P4VP$_{21k}$ and PS$_{62k}$P4VP$_{66k}$ surfaces in FIG. 5a are indistinguishable from the spectrum of PS homopolymer. Thus, the un-quaternized block copolymer surfaces are almost completely covered by the lower surface-energy PS block, which fully supports the interpretation of the contact angle results.

Using PS-b-P4VP block copolymers in which the P4VP block was end-functionalized with 3,3,3-trifluoropropyldimethylchlorosilane, Jiang et al. found that the P4VP block segregated to the surface because of the low surface-energy —CF$_3$ group at its end (*Polymer* 1998, 39, 2615-2620). However, the PS$_{11k}$P4VP$_{21k}$ and PS$_{62k}$P4VP$_{66k}$ block copolymers used in our study did not show surface segregation of the higher surface-energy block, even though the P4VP blocks were terminated with perfluorooctyl groups. The reason for the difference probably lies in the fact that the block copolymer studied by Jiang and coworkers had a relatively low molecular weight (14 kDa total) compared to those used in the present study. A single perfluorooctyl group at the end of our longer P4VP blocks was unable to bring these to the surface.

To displace the PS block from the surface, the decrease in P4VP block surface energy contributed by the perfluorooctyl groups must compensate for the increased energy of the exposed P4VP surface. This compensation will require a high areal density of perfluorooctyl groups resulting in the necessity of the P4VP chains to stretch away from the surface. The free energy penalty for the required P4VP stretching increases as the P4VP block length increases and, thus, above some block length, the perfluorooctyl end group will be ineffective in bringing the P4VP block to the surface.

While the PS$_{62k}$P4VP$_{66k}$ block copolymer surface did not show any N 1 s signal, the 4-vinylpyridine block could be detected in the N 1s NEXAFS spectrum of the PS$_{11k}$P4VP$_{21k}$ polymer. However, these resonances were much weaker in intensity compared to the P4VP homopolymer (cf. FIG. 4b). The radius of gyration of PS with a molecular weight of 62 kDa can be estimated to be about 7 nm (see Cotton et al. *Macromolecules* 1974, 7, 863-872). The thickness of the PS layer covering the 4VP block is expected to be at least 7 nm, which is large compared to the expected escape depth of the N 1 s Auger electrons from the surface. Hence, if the P4VP block is buried below a layer of PS chains, it would not be detected, as observed experimentally for the PS$_{62k}$P4VP$_{66k}$ surface.

The radius of gyration of PS with a molecular weight of 11 kDa is about 2.9 nm, comparable to the escape depth of the N 1 s Auger electrons. Thus, some detection of the Auger electrons resulting from N 1 s transitions would be expected for the PS$_{11k}$P4VP$_{21k}$ surface, as seen experimentally.

When the PS-b-P4VP polymer is quaternized with 1-bromohexane, the lower surface energy —CH$_3$ and —CH$_2$— groups of the alkyl side chains would be thermodynamically favored at the air-polymer interface over the phenyl rings of the PS block. In contrast to the un-quaternized polymers, the presence of the pyridinium block at the surface is evident from the NEXAFS spectra of FIG. 5(c and d). The N 1 s resonances are higher in intensity, compared to the spectra in FIG. 5b, especially in the case of the PS$_{62k}$P4VP$_{66k}$H6Br surface. The spectra of the block copolymers with different molecular weights, PS$_{11k}$P4VP$_{21k}$H6Br and PS$_{62k}$P4VP$_{66k}$H6Br, now become almost identical. The N 1 s resonances in the NEXAFS spectra of the quaternized diblock copolymers were, however, lower in intensity than those for the homopolymer P4VP$_{60k}$H6Br due to the presence of some phenyl rings at the surface (cf. FIG. 4b and FIG. 5d). The effect of PS block at the surface is also evident in the higher intensity of the C 1 s→π* resonance intensity compared to the P4VP$_{60k}$H6Br homopolymer (cf. FIG. 4a and FIG. 5c).

NEXAFS analysis of the surfaces used for bacterial tests. The C 1 s and N 1 s NEXAFS spectra of the surfaces used in the bacterial assays are shown in FIG. 6 and FIG. 7. These surfaces were prepared by spray-coating the quaternized polymers on SEBS covered glass microscope slides, as previously discussed. FIG. 6 compares the NEXAFS spectra of the fluorinated and non-fluorinated pyridinium diblock copolymers, $PS_{62k}P4VP_{66k}(F8H6_{0.3}H6)Br$ and $PS_{62k}P4VP_{66k}H6Br$, respectively. The differences in the NEXAFS spectra of the $PS_{62k}P4VP_{66k}H6Br$ surfaces prepared by the spin-coating (FIG. 5) and the spray-coating (FIG. 6) techniques are attributed to the different processing conditions used for the two surfaces. The spin-coated samples were annealed at 150° C., which is above the glass transition temperature of the polystyrene block, while the spray-coated samples were dried at 60° C.

The 1 s→σ*$_{C-F}$ resonance in the C 1 s spectrum of $PS_{62k}P4VP_{66k}(F8H6_{0.3}H6)Br$, near 293 eV in FIG. 6a, showed the presence of the semifluorinated alkyl group, and hence the pyridinium block, at the surface. The intensity of the σ*$_{C-F}$ resonance was independent of the X-ray incident angle. Hence, the semifluorinated side groups were not oriented the surface. The N 1 s resonances, and also the edge jump, were higher in intensity for the fluorinated pyridinium block copolymer surface than the corresponding non-fluorinated polymer (cf. FIG. 6b), indicating a higher surface concentration of pyridinium rings in the former surface.

To investigate the effect of molecular weights of the PS and P4VP blocks on the surface composition of the quaternized polymers, the intensities of the carbon and nitrogen K-edge resonances were compared. For both the non-fluorinated and fluorinated $PS_{11k}P4VP_{21k}$ and $PS_{62k}P4VP_{66k}$ pyridinium block copolymers, (i) the intensity of the C 1 s→π* transition was higher in the case of the higher molecular weight polymers, and (ii) the edge jump and the N edge resonances were lower in intensity for the higher molecular weight polymers. These observations indicate that the surface concentration of polystyrene units was higher in the case of the $PS_{62k}P4VP_{66k}$ polymers than the $PS_{11k}P4VP_{21k}$ polymers. Also, as seen from FIG. 6b, the surface concentration of $N^+$ atoms is higher for the fluorinated $PS_{61k}P4VP_{66k}$ surface.

FIG. 7 compares the NEXAFS spectra of the $P(4VP-r-BMA)_{300k}$ and $P(4VP-r-BMA)_{300k}$ H6Br surfaces. The absence of the 7 peak corresponding to un-quaternized pyridine rings in the N 1 s spectrum, reflects the almost complete quaternization of the precursor polymer, which is in accord with the results from IR spectroscopy.

X-ray Photoelectron Spectroscopy of Surfaces used for Antibacterial Tests

The relative numbers of carbon and nitrogen atoms at the surfaces of the pyridinium polymers used in the antibacterial assays were also compared using XPS. Bilayer coatings were prepared by spray coating the polymers on SEBS covered glass slides, followed by drying at 60° C. in vacuum to remove solvent. All XPS data were collected with a 0° electron emission angle (along the surface normal). FIG. 8 shows the N 1 s XPS spectra for the P4VP homopolymer before and after quaternization with 1-bromohexane. Upon quaternization, the nitrogen peak shifted to a higher binding energy. The small peak at 399 eV is due to the nitrogen atoms that had not undergone the quaternization reaction. By comparing the areas under the two peaks, the percentage of nitrogen atoms that were quaternized could be calculated. As seen in Table 3, all the pyridinium polymers showed a high degree of quaternization.

TABLE 3

Percent of pyridinium groups quaternized.

| Polymer | % Quaternization |
|---|---|
| $P4VP_{60k}$ | 0 |
| $P4VP_{60k}H6Br$ | 95.2% |
| $PS_{11k}P4VP_{21k}H6Br$ | 95.5% |
| $PS_{62k}P4VP_{66k}H6Br$ | 90.9% |
| $PS_{11k}P4VP_{21k}(F8H6_{0.3}H6)Br$ | 93.1% |
| $PS_{62k}P4VP_{66k}(F8H6_{0.3}H6)Br$ | 94.3% |

The C 1 s XPS spectra of the fluorinated pyridinium block copolymers (FIG. 9a) showed distinct —$CF_2$— and —$CF_3$ peaks at binding energies of 292 eV and 294 eV, respectively. Although a small number of C—F carbon atoms from the perfluorooctyl end groups of the PS-b-P4VP precursors (cf. block copolymer 1 in Scheme 1) are expected to be present in the otherwise non-fluorinated $PS_{11k}P4VP_{21k}H6Br$ and $PS_{62k}P4VP_{66k}H6Br$ surfaces, the low intensity peaks seen near 292 eV in FIG. 9b are the shake-up peaks. The shoulder at 286 eV is characteristic of carbon atoms bonded to nitrogen atoms (see Cen et al. *Langmuir* 2003, 19, 10295-10303).

The areas under the C—N peaks were lower for the non-fluorinated block copolymers than the fluorinated polymers, suggesting a higher concentration of quaternary nitrogen in the fluorinated surfaces. Moreover, the areas of the N 1 s peaks near 402 eV (FIG. 9c and FIG. 9d) were correspondingly lower for the non-fluorinated polymers. Thus, the lower molecular weight polymers had more $N^+$ atoms at the surface than their higher molecular weight counterparts, and the fluorinated polymers had more quaternized nitrogen at the surface than the non-fluorinated pyridinium block copolymers.

The results of NEXAFS spectroscopy and XPS may be summarized as follows. Quaternization of PS-b-P4VP with 1-bromohexane resulted in the presence of the higher surface energy P4VP block at the surface, which was otherwise buried below the PS block. The relative number of NW atoms at the surface was further enhanced when 6-perfluorooctyl-1-bromohexane was used. Partial quaternization of PS-b-P4VP with F8H6Br resulted in a higher surface concentration of $N^+$ compared to block copolymers alkylated using H6Br alone. The $PS_{62k}P4VP_{66k}$ block copolymers with higher weight fractions of PS, showed higher surface concentrations of PS.

Antibacterial Assay. The antibacterial activity of the pyridinium surfaces were evaluated by performing a viable count on *S. aureus* cells sprayed onto the surfaces. As seen in FIG. 10A, a large number of bacterial colonies formed on the untreated glass slide, which is not expected to have any bactericidal activity.

Assuming that the same number of *S. aureus* cells were sprayed onto the glass control and test surfaces, the relative number of colonies on the glass and test surfaces represents the fraction of the sprayed cells that remained viable on the test surfaces. The viable counts were 15 to 30% lower on the $PS_{11k}P4VP_{21k}H6Br$ (FIG. 10B) and $PS_{62k}P4VP_{66k}H6Br$ (FIG. 10C) surfaces compared to the glass control. While the non-fluorinated diblock copolymers had a large number of bacterial colonies, only somewhat lower than that on uncoated glass, the fluorinated pyridinium polymers (FIG. 10E and FIG. 10F) showed an almost 100% decrease in the viable count. The lengths of the pyridinium blocks in both the sets of polymers were the same, but quaternization with F8H6Br caused a significant increase in the bactericidal activity of the surfaces.

The enhanced activity is attributed to the differences in surface compositions and molecular organizations. Both NEXAFS spectroscopy and XPS showed that the surface concentration of the pyridinium rings, and hence the surface charge density, was higher in the case of the fluorinated polymers, which is also consistent with the lower water contact angles observed for these surfaces. A higher charge density is expected to result in stronger electrostatic interactions between the cells and the surface, which in turn would lead to cell death by various mechanisms. The concentration of pyridinium rings, however, cannot be the only factor affecting antibacterial activity. The surface concentration of the quaternary nitrogen was higher for $PS_{11k}P4VP_{21k}H6Br$ than $PS_{62k}P4VP_{66k}(F8H6_{0.3}H6)Br$. However, the bactericidal effect of the non-fluorinated surface was significantly lower. It is not known conclusively whether the rigid and highly hydrophobic perfluoroalkyl helices have a greater ability to disrupt the bacterial cell membrane. Nevertheless, the non-polar nature and a rod-like conformation of the fluoroalkyl helices could be responsible for the higher antibacterial activity of the fluorinated surfaces.

The viable count for the relatively high molecular weight $P(4VP-r-BMA)_{300k}H6Br$ polymer (FIG. 10D) was 60±12% lower than that on glass. Despite its high molecular weight, its bactericidal efficiency was less than that of the $PS_{11k}P4VP_{21k}(F8H6_{0.3}H6)Br$ and $PS_{62k}P4VP_{66k}(F8H6_{0.3}H6)Br$ surfaces. This suggests that in addition to molecular weight, the molecular organization at the surface played a crucial role in antibacterial activity. The reason for the reduced activity was partially evident from the contact angle measurements. The advancing water contact angle on the spray-coated surface of the $P(4VP-r-BMA)_{300k}H6Br$ polymer was about 99°. Such a high angle is indicative of a very dense layer of alkyl groups covering the pyridinium rings, which is believed to be unfavorable for bactericidal activity.

The *S. aureus* cells used in the antibacterial assays were in the exponential phase of growth and capable of cell division. The lower number of bacterial colonies on the pyridinium surfaces could be either through interference with cell division, or by causing major disorganization of the cell membrane resulting in cell death. The BacLight staining method confirmed that the test surfaces caused disruption of the cell membrane within 15 min of contact. BacLight employs two nucleic acid stains: the green-fluorescent SYTO® 9, which has excitation and emission maxima at 480 nm and 500 nm, respectively, and the red-fluorescent propidium iodide (PI), which has excitation and emission maxima at 537 nm and 620 nm, respectively. See Biggerstaff et al. *Molecular and Cellular Probes* 2006, 20, 141-146; and Boulos et al. *J. Microbiol. Meth.* 1999, 37, 77-86.

Besides their spectral characteristics, SYTO® 9 and PI have different abilities to penetrate bacterial cell membranes and different binding affinities toward nucleic acids. SYTO® 9 can freely permeate intact cell membranes. It is essentially non-fluorescent in the free-state, but its fluorescence quantum yield increases by 1000-fold or more upon binding to nucleic acids. In contrast, PI penetrates only cells with damaged membranes. Propidium iodide has a higher affinity toward nucleic acids, displaces the less strongly bound SYTO® 9 thereby reducing the intensity of the green fluorescence, and itself fluoresces red. The fluorescence quantum yield of PI increases 20-30 fold upon binding to nucleic acids. Thus, by the suppression of the intensity of green fluorescence and an enhancement in the red fluorescence, bacteria with damaged membranes appear red while those with intact membranes appear green.

*S. aureus* cells on an uncoated glass slide and on a glass slide coated with the $P(4VP-r-BMA)_{300k}H6Br$ polymer were stained. Cells with intact cell membranes were stained green and those with damaged membranes are stained red. Almost all of the cells on the glass control were stained green, indicating intact and possibly viable cells. The cells on the surface of the quaternized polymer were stained red, suggesting disruption of the cell membrane. Thus, the antibacterial activity of pyridinium surfaces seems to be through the loss of membrane integrity, rather than inhibition of cell division.

Conclusions. Pyridinium block copolymers with fluorinated side chains were synthesized by quaternization reaction of a semifluorinated alkyl bromide with polystyrene-block-poly(4-vinylpyridine). Surfaces of the fluorinated block copolymers were found to be more effective in decreasing the viability of airborne *Staphylococcus aureus* than N-hexyl pyridinium surfaces. NEXAFS and contact angle measurements showed that fluorination resulted in an increase in the number of pyridinium rings at the surface which, in general, correlated with a higher antibacterial activity. In addition, the fluoroalkyl side chains may be intrinsically favorable for disruption of the bacterial cell membrane due to their rigidity and hydrophobicity.

Surfaces with a dense layer of alkyl side chains covering the pyridinium groups showed higher water contact angles, lower N 1 s signals in NEXAFS spectroscopy, and were found to exhibit lower antibacterial activity. In contrast, when alkyl (or fluoroalkyl) side groups were not densely packed and the surface concentration of the pyridinium nitrogen was sufficiently high, a greater antibacterial activity was observed. Molecular weight does not seem to be a limiting factor in determining antibacterial activity. The fluorinated pyridinium block copolymer with a relatively low P4VP block molecular weight of 21 kDa (degree of polymerization 200), showed almost 100% bactericidal effect. The pyridinium surfaces were also found to inhibit the growth of spores of the marine alga *Ulva linza* when immersed in seawater (see Krishnan et al. *Polymer Preprints* (*American Chemical Society, Division of Polymer Chemistry*) 2005, 46, 1248-1249).

Example 3

Interaction of *Ulva* and *Navicula* Marine Algae with Surfaces of Pyridinium Polymers with Fluorinated Side-Chains Introduction: The formation of a microbial biofilm of bacterial cells, algal spores, diatoms and protozoa is an important initial step in the marine biofouling process. Surfaces prepared using quaternized 4-vinylpyridine polymers are antibacterial and can prevent the formation of bacterial biofilms. The antibacterial activity of these polymers is believed to arise from the cationic binding of the cell membrane, resulting in a disruption of the membrane and subsequent leakage of the cytoplasmic materials. *Ulva* zoospores and *Navicula* diatoms are microalgae commonly encountered in biofilms that develop on ship-hulls. Both are unicellular organisms and attach to surfaces through extracellular polymeric substances (EPS) that are adhesive in nature.

Settlement of a free-swimming *Ulva* zoospore on a surface is influenced by physico-chemical properties of the surface (such as chemical composition and wettability) and surface topography. Adhesion is achieved by the secretion of a hydrophilic glycoprotein that crosslinks rapidly after release from the spore.

The work reported in this Example investigated whether 4-vinylpyridinium polymers that formed bactericidal surfaces could also function as marine antifouling surfaces. Polystyrene-block-poly(4-vinylpyridine) (PS/P4VP) was quaternized with alkyl and fluoroalkyl bromides, and surface-activity against *Ulva* and *Navicula* was studied. The number of *Ulva* zoospores and *Navicula* cells settling and attaching to the these surfaces was determined and compared to hydrophobic poly(dimethyl siloxane) and hydrophilic glass controls. A block copolymer with fluoroalkyl side chains, but without the positive charge of the 4-vinylpyridinium polymers was also studied. The adhesion strengths of algal cells were characterized by the degree of removal under water shear stress in a turbulent flow channel.

Experimental. Scheme 5 shows three types of surface-active block copolymers that were studied. Polystyreneblock-poly(4-vinylpyridine) (PS/P4VP) block copolymers were synthesized by anionic polymerization (Krishnan et al. *Polym. Mater. Sci. Eng.* 2004, 91, 814). Polymers with PS and P4VP block molecular weights of 11 kDa/21 kDa and 62 kDa/66 kDa were quaternized with co-6-perfluorooctyl-bromohexane and 1-bromohexane to obtain block copolymers with semifluorinated side chains (I).

Scheme 5. Surface-active block copolymers (SABC) tested for interactions with marine algae Ulva and Navicula.

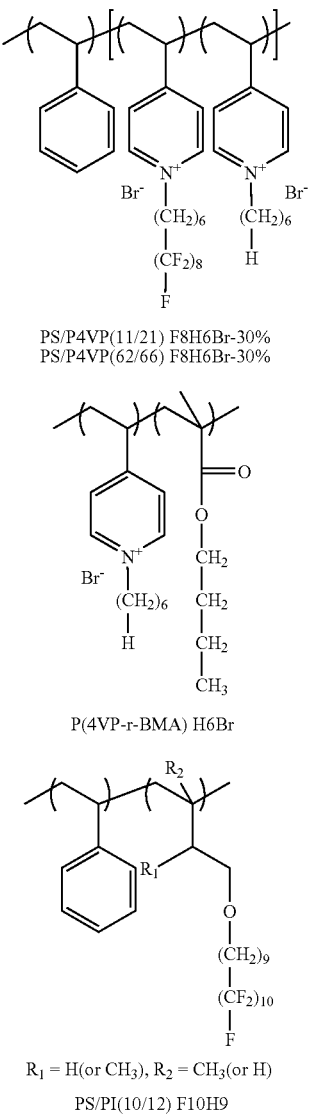

PS/P4VP(11/21) F8H6Br-30%
PS/P4VP(62/66) F8H6Br-30%

P(4VP-r-BMA) H6Br $R_1$ = H(or $CH_3$), $R_2$ = $CH_3$(or H)

PS/PI(10/12) F10H9

Synthesis of semifluorinated alkyl bromide. Three grams (5.77 mmol) of co-6-perfluorooctyl-hexanol and 3 g (9.05 mmol) of $CBr_4$ were dissolved in a mixture of 6 mL anhydrous THF and 12 mL anhydrous methylene chloride and cooled to –5° C. Triphenylphosphine (2.37 g, 9.05 mmol) was then added in small portions over a period of 15 minutes. After stirring for 1 hour at –5° C. and 6 hours at room temperature, solvent was evaporated from the reaction mixture under vacuum, and ca. 50 mL diethyl ether was added. The insoluble solid (triphenylphosphineoxide byproduct) was separated by filtration, and the filtrate concentrated to obtain the crude product that was purified by passing through a short silica gel column with diethyl ether as the elution solvent.

Quaternization using ω-6-perfluorooctyl-bromohexane. One gram (4.92 mmol 4-VP) of the PS/P4VP block copolymer (62 k/66 k) and 0.8630 g (1.48 mmol) of ω-6-perfluorooctyl-bromohexane were dissolved in 10 mL of DMF and heated to 80° C. for ca. 24 hours. 1-Bromohexane (5.88 g, 35.6 mmol) was added and the reaction was continued further for 24 hours at 80° C. After cooling to room temperature the polymer was precipitated in diethyl ether at 0° C. PS/P4VP (62/66)F8H6Br-30% was prepared by reacting 30 mol % of $F(CF_2)_8(CH_2)_6Br$ (based on 4-VP) with the 62 k/66 k PS/P4VP block copolymer. PS/P4VP(11/21)F8H6Br-30% and PS/P4VP(62/66)F8H6Br-50% block copolymers were similarly prepared. A random copolymer of 4-VP and n-butylmethacrylate copolymer with a molecular weight of 300,000 g/mol and 10 wt % BMA were also quaternized with 1-bromohexane (II).

Side-chain liquid crystalline block copolymers with semifluorinated groups (III) were prepared by polymer analogous reactions on polystyrene-block-poly(isoprene) (PS/PI) copolymer with block molecular weights of 10 kDa/12 kDa. The procedure described Wang and co-workers (*Macromolecules* 1997, 30, 1906) was used to prepare the PS/PI(10/12) F10H9 block copolymer. The block copolymers were characterized by IR spectroscopy on a KBr salt plate.

Preparation of test surfaces. Bilayer coatings were prepared by spray-coating the block copolymer solutions on a glass microscope slide coated with a PS-block-poly(ethylene-ran-butylene)-block-PS thermoplastic elastomer (SEBS, Kraton G1652). The PS blocks in the bottom (SEBS) and top (SABC) layers are expected to mix at the interface, welding the two layers. 1.5% (w/v) solutions of the quaternized polymers in chloroform (or chloroform-methanol mixture), and 2% (w/v) solution of (III) and SEBS (9:1 mass ratio) in α,α,α-trifluorotoluene and toluene (2:1 volume ratio) were used for spray-coating. The former surfaces were dried in vacuum at 60° C., and the PS/PI(10/12)F10H9 surfaces annealed at 120° C. for 24 hours.

Algal Assays. Fertile plants of *Ulva linza* were collected from Wembury beach, UK (50°18'N; 4°02'W). Zoospores were released and treated as described by Wang and co-workers (ibid.). Each slide was exposed to 10 mL of a $1.5 \times 10^6$ spore/mL suspension in seawater for 1 hour. Settled zoospores were counted. Adhered zoospores were cultured for 10 days to produce sporelings (young plants), and the resulting biomass was quantified by measurement of the chlorophyll a content. To measure the attachment strength of the sporelings, biomass was determined before and after applying a wall shear-stress of 53 Pa in a flow channel. Assays with diatoms (*Navicula*) were set up as described by Holland and co-workers *Biofouling* 2004, 20, 323) Attachment strength was measured in a flow channel and percentage removal calculated as above.

Results and Discussion:

Settlement, Growth and Release of *Ulva* and *Navicula*. FIG. 11 shows the settlement and growth of *Ulva* zoospores on the pyridinium and isoprene based block copolymers with semifluorinated side chains. Although settlement was significantly higher on the pyridinium surface compared to PDMS or glass (cf. FIG. 11a), the growth of sporelings was lower (cf. FIG. 11b). Considering the fact that the PS/P4VP(11/21) F8H6Br-30% surface was hydrophilic (advancing and receding water contact angles of ca. 56° and 7°, respectively), high settlement on this surface is opposite of what is expected from previous results on the influence of surface wettability on settlement of *Ulva*. Using alkane thiols terminated with methyl and hydroxyl groups, and mixtures of the two, Finlay et al. found that settlement of *Ulva* was greatest on a hydrophobic surface (Finlay et a. *Integr. Comp. Biol.* 2002, 42, 1116).

An important difference between the $CH_3$ and OH self-assembled monolayers and the pyridinium surface is that the latter is charged. Favorable electrostatic interactions between the negatively charged spores (or the EPS) and the polymer surface could have promoted spore-settlement, but their growth was inhibited, possibly due to the antimicrobial activity of the surface. The non-polar PS/PI(10/12)F10H9 surface with advancing and receding water contact angles of 123° and 85°, respectively, on the other hand, showed lowest settlement and growth, and a relatively high biomass-removal of ca. 70% (compared to ca. 24% from the pyridinium surface and ca. 11% from glass).

From a study using PEGylated and fluorinated (III) block-copolymer surfaces, we found that the adhesion strength of *Navicula* diatoms was lowest on a hydrophilic surface, which concurs with previous observations (see Holland et al. *Biofouling* 2004, 20, 323). However, as seen from FIG. 12, the adhesion to some of the hydrophilic pyridinium surfaces was stronger in comparison to the hydrophobic PS/PI(10/12) F10H9. This could again be attributed to electrostatic interactions, which are absent in fluorinated and PEGylated surfaces.

Conclusions. The settlement of *Ulva* zoospores on the PS/PVP(11/21)F8H6Br-30% surface was unexpectedly high, possibly due to electrostatic interactions between the spores and the surface. However, this surface inhibited the growth of spores, and the amount of biomass after a 10-day growth period was lower than that on PDMS or glass. Release of settled *Navicula* diatoms was easier from the relatively high molecular weight P(4VP-co-BMA)H6Br and the PS/PI(10/12)F10H9 surfaces compared to PDMS. The pyridinium surfaces are expected to show a stronger antimicrobial effect against *Ulva* compared to *Navicula* whose cells are surrounded by a protective siliceous cell wall (frustules).

Example 4

Pyridinium Polymers with PEGylated and Semifluorinated Side Groups

Pyridinium block copolymers with ω-6-perfluorooctyl-bromohexane and 1-bromohexane side chains have shown promising antibacterial activity against the air-borne pathogen, *S. aurues*. They have also shown antimicrobial activity against *Ulva* zoospores, inhibiting the growth of sporelings. Scheme 6 shows the structure of the amphiphilic pyridinium block copolymer with PEG and fluoroalkyl side chains. The pyridinium block copolymer is illustrated with mixed semi-fluorinated and PEGylated side groups. A $PS_{62k}P4VP_{66k}$ diblock copolymer was used. About 30% of the pyridine groups were quaternized with semifluorinated alkyl bromide and the remaining with PEG bromide.

The amphiphilic character was evident from the water contact angle measurements, which were highly dependent on the temperature at which the surfaces were annealed (Table 4). A 3% (w/v) solution of the block copolymer in chloroform was used, and the surfaces were annealed at 120° C. or 60° C. in vacuum for 12 hours.

TABLE 4

Advancing and receding water contact angles

|  | Anneal temp. | $\theta_A$ | $\theta_R$ |
|---|---|---|---|
| Spin-coated | 120° C. | 102° | 9° |
| Spin-coated | 60° C. | 71° | 11° |
| Spray-coated | 60° C. | 91° | 9° |

The relatively high advancing angle and the low receding angle suggest the presence of the pyridinium block at the surface. The low receding water contact angle is due to the ionic pyridinium groups and the hydrophilic PEG chains. XPS spectra of the spray-coated surface are shown in FIG. 13. The high resolution C1 s spectra were obtained at electron emission angles of 0° and 75° with respect to surface normal. A higher surface concentration of $CF_2$ and $CF_3$ groups is evident from the 75° emission angle spectrum, which probes thinner surface layers than 0° emission.

The pyridinium surfaces were found to be water sensitive due to a high content of hydrophilic PEG groups, in addition to the ionic nature of the pyridinium rings. The polymer shown in Scheme 6 does not have n-hexyl side chains. Current understanding of antibacterial activity of pyridinium polymers is that the groups attached to the pyridinium ring should have an optimal hydrophilic-lipophilic balance to penetrate the lipid bilayer of bacterial cell membrane. A higher fluoroalkyl content should improve water resistance, and antifouling performance.

Example 5

Free Radical Polymerization Methods

Anionic polymerization to synthesize polystyrene-block-poly(4-vinylpyridine) block copolymers was discussed above. The anionic mechanism allowed relatively rapid polymerization and facile end-functionalization of the 4VP block with (heptadecafluoro-1,1,2,2-tetrahydrodecyl)dimethylchlorosilane. However, the polymerization reaction is highly air- and moisture-sensitive and rather stringent purity of Scheme 6.

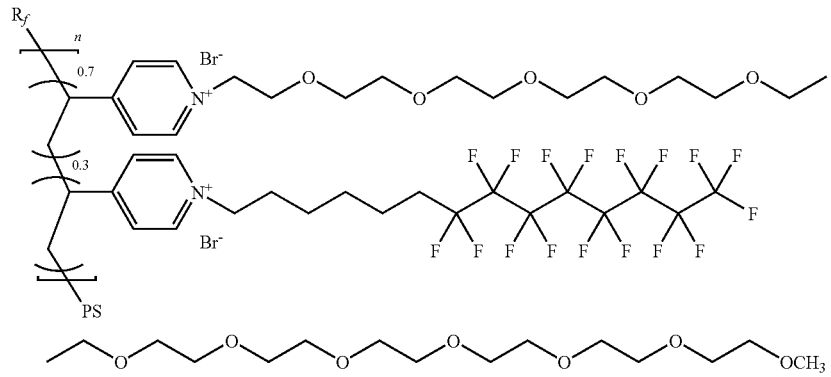

chemicals is required. Controlled free radical polymerization, possibly more versatile than anionic polymerization, can also be used to prepared the polymers of the invention, including those containing 4-vinylpyridine groups.

Polystyrene-block-poly(4-vinylpyridine-co-styrene) was prepared by nitroxide mediated controlled free radical polymerization. Benzoyl peroxide and TEMPO were used as the initiator and capping agent (stabilizer), respectively, in the synthesis of the PS macroinitiator (Scheme 7). The PS block mol. wt. was about 20,000 g/mol. The PS macroinitiator was then used to copolymerize styrene and 4-vinylpyridine to obtain polystyrene-block-poly(4-vinylpyridine-ran-styrene) diblock copolymer. The P(4VP-r-S) block had a molecular weight of about 70,000 g/mol, and consisted of about 30 mol % styrene and 70 mol % 4-vinylpyridine. The pyridine groups were quaternized with 1-bromohexane.

Surfaces prepared from solutions of this polymer in chloroform or chloroform-methanol mixture showed good antibacterial activity against S. aureus. Moreover, spray-coated surfaces of this polymer did not cloud upon exposure to water, and hence can also be used as a marine anti-bactericidal coating.

FIG. 14 compares the NEXAFS spectra of spray-coated bilayer coatings of different pyridinium polymers on SEBS substrates. Of these, the polymer $PS_{20k}P(4VP_{0.7}\text{-r-}S_{0.3})_{70k}$H6Br was obtained from block copolymer precursor synthesized using nitroxide mediated polymerization. The N 1 s resonances were higher in intensity in the case of the $PS_{20k}P(4VP_{0.7}\text{-r-}S_{0.3})_{70k}$H6Br compared to the fluorinated and non-fluorinated $PS_{62k}P4VP_{66k}$ pyridinium surfaces. Thus, the surface concentration of pyridinium rings is higher for $PS_{20k}P(4VP_{0.7}\text{-r-}S_{0.3})_{70k}$H6Br, which is expected to impart good antibacterial activity.

Controlled free radical polymerization of 4-vinylpyridine can be carried out using any of the several nitroxide initiator systems reported in the literature, for example, N-tert-butyl-N-(1-diethylphosphono-2,2,-dimethyl)propyl nitroxide (DEPN, 1) with 2,2'-azobisisobutyrlnitrile (AIBN), or the unimolecular initiators (2) and (3) (Scheme 8). See Benoit et al. *J. Am. Chem. Soc.* 2000, 122, 5929-5939; and Hawker et al. *Chem. Rev.* 2001, 101, 3661-3688, respectively for DEPN and unimolecular inhibitors, respectively. Lee et al. have recently reported a reversible addition-fragmentation chain transfer (RAFT) method to prepare polystyrene-block-poly(4-vinylpyridine). See *Polymer* 2006, 47, 3838-3844.

Scheme 7. Synthesis of pyridinium block copolymers using controlled free radical polymerization.

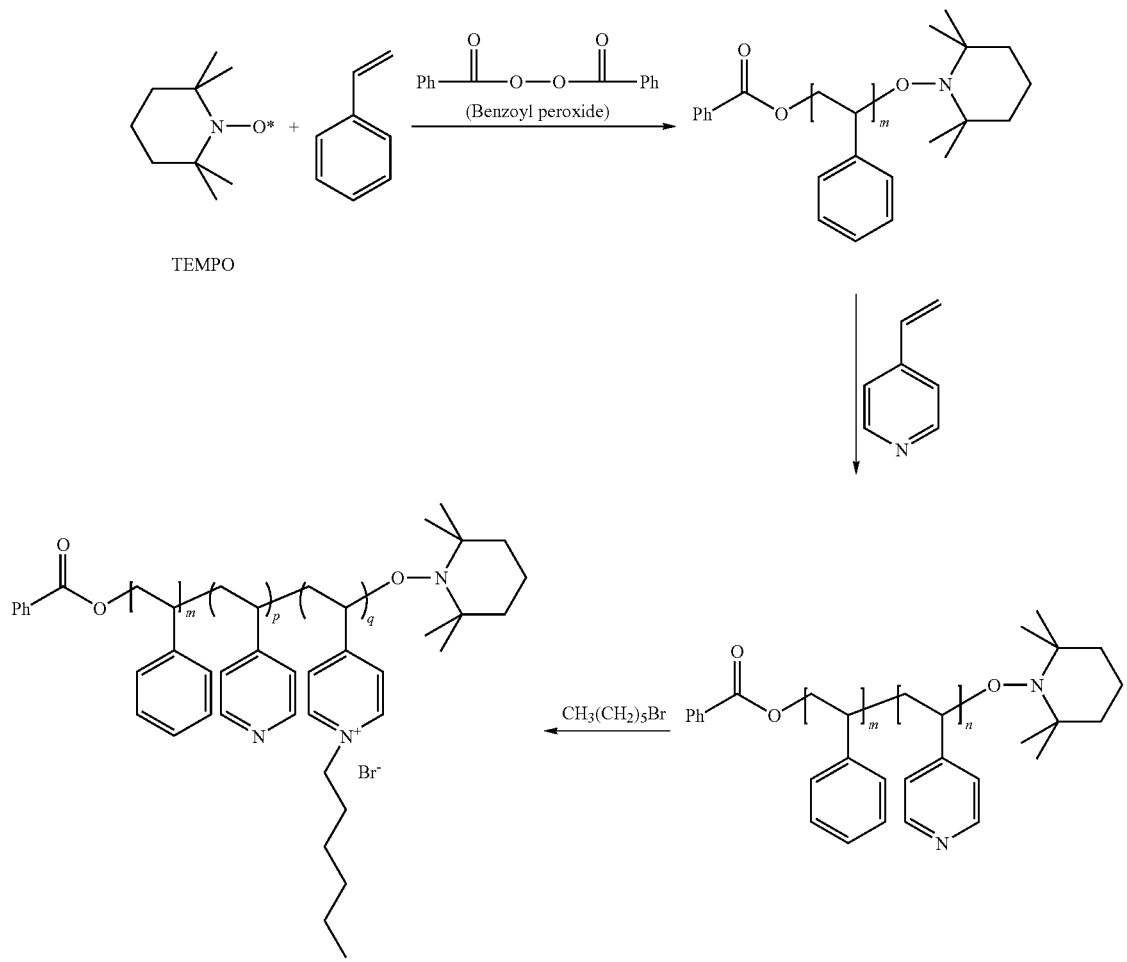

Scheme 8. Nitroxide stabilizers and unimolecular initiators commonly used for nitroxide-mediated free radical polymerization.

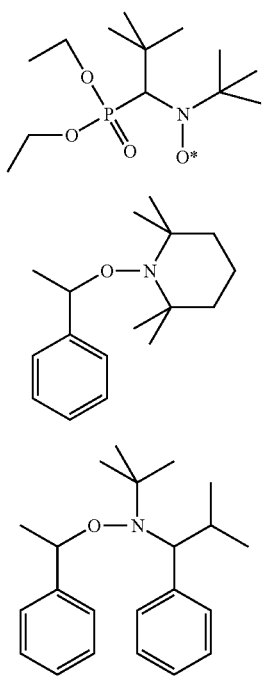

End-functionalization with semifluorinated groups can be achieved by growing a short third block of fluorinated monomer as shown in Scheme 9, where Rf is a semifluorinated alkyl group.

Scheme 9. Polystyrene-block-poly(4-vinylpyridine) end functionalized with a short fluorinated segment.

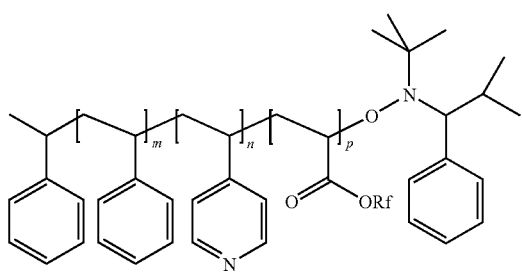

The structure shown in Scheme 9 would be obtained if the unimolecular initiator 3 (Scheme 8) were used in the triblock copolymer synthesis.

Example 6

Marine antifouling characteristics of poly(N-hexylpyridinium bromide-ran-n-butyl methacrylate), P(4VP-r-BMA)$_{300k}$H6Br, evaluated using the green alga, *Ulva*

Polymer synthesis. Six grams of poly(4-vinylpyridine-ran-butyl methacrylate), with a molecular weight of 300 kDa and 10 wt % of n-butyl methacrylate, was reacted with 8 mL of 1-bromohexane in 60 mL of nitromethane at 80° C. for 2 days followed by precipitation of the polymer in diethyl ether, as illustrated in Scheme 10.

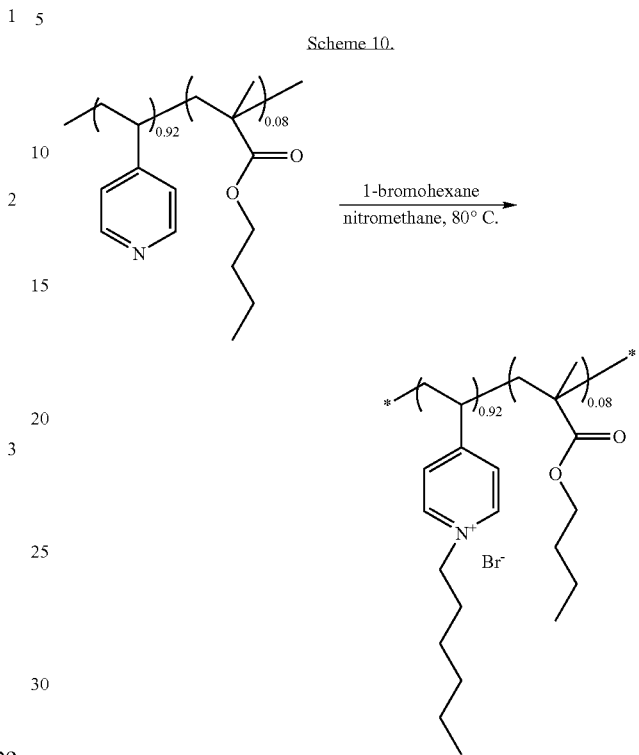

Preparation of test surfaces. Surfaces were prepared on 3 inch×1 inch glass microscope slides. To improve adhesion of the pyridinium polymer to glass, polystyrene-block-poly(ethylene-ran-butylene)-block-polystyrene (Kraton SEBS G1652) was first spin-coated on the glass slides using a 10% (w/v) solution in toluene and annealed in a vacuum oven at 120° C. for 12 hours. A 1.5% (w/v) solution of P(4VP-r-BMA)$_{300k}$H6Br was then sprayed on the SEBS-coated glass slides (heated to 80° C. on a hot-plate) using a Badger Model 250 airbrush (50 psi nitrogen gas pressure). About 3 mg of the pyridinium polymer was used per cm$^2$ of the surface. The spray-coated surfaces were dried in a vacuum oven at 60° C. for 24 hours. Surfaces of unquaternized random copolymer P(4VP-r-BMA)$_{300k}$ were similarly prepared to be used as controls.

*Ulva* assays. Slides were leached for 6 days in circulating de-ionized water and immersed in seawater for one hour before the start of the experiment. Fertile plants of *Ulva linza* were collected from Wembury Beach, England (50° 18' N; 4° 02' W). Zoospores were released and prepared for attachment experiments as described by Callow et al. (*J. Phycol.* 1997, 33, 938-947). Slides (3 replicates) were settled with spores using the same stock and concentration of spores that were used for the sporeling studies (6 replicates). Ten-milliliter of zoospore suspensions were pipetted into individual compartments of polystyrene culture dishes (Fisher), each containing a glass microscope slide. The dishes were incubated in the dark at about 20° C. After 1 hour the slides were gently washed in seawater to remove zoospores that had not attached. The density of zoospores attached to the surface was counted on each of 3 replicate slides using an image analysis system attached to a fluorescent microscope. Spores were visualized by autofluorescence of chlorophyll. Counts were made for 30 fields of view (each 0.17 mm²) on each slide.

Growth of sporelings. Spores were allowed to settle for 1 hour in darkness. After washing, sporelings were cultured in enriched seawater medium in individual (10 mL) wells in polystyrene dishes under illuminated conditions. The medium was refreshed every 2 days and the sporelings cultured for 7 days. Strength of attachment of sporelings was assessed by exposing single slides of each treatment to the water jet at a range of water pressures. Sporeling biomass was determined in situ by measuring the fluorescence of the chlorophyll contained within the sporelings that covered the slides, in a Tecan fluorescent plate reader. Using this method the biomass was quantified in terms of relative fluorescent units (RFU). The RFU value for each slide is the mean of 70 point fluorescence readings. Acid washed glass slides and PDMS surfaces (T2 Silastic) were also included as standards.

Navicula assays. Navicula cells were cultured in F/2 medium contained in 250 ml conical flasks. After 3 days the cells were in log phase growth. Cells were washed 3 times in fresh medium before harvesting and diluting to give a suspension with a chlorophyll a content of approximately 0.3 μg/mL. Cells were settled in individual dishes containing 10 mL of suspension in natural daylight at ~20° C. After 2 hours the slides were very gently washed in seawater to remove cells which had not properly attached. The density of cells attached to the surface was counted on each slide using an image analysis system attached to a fluorescent microscope. Counts were made for 30 fields of view (each 0.064 mm²) on each slide.

Strength of attachment. Slides settled with Navicula were exposed to shear stresses in a water channel. Glass and PDMS standards were included. The number of cells remaining attached was compared with unexposed control slides (used to determine attachment as above). On most surfaces the cells were counted using the image analysis system as described above.

Toxicity. An additional slide of each treatment was inoculated with cells of Navicula and grown for 3 days in an illuminated cabinet. Observations were made at 24 hour intervals.

Results and Discussion: Ulva assays. The coatings were not affected after a six day immersion in water and remained firmly adhered to glass substrates. FIG. 15 shows the spore settlement density on glass, PDMS, the unquaternized P(4VP-r-BMA)$_{300k}$, and the quaternized P(4VP-r-BMA)$_{300k}$ H6Br surfaces. The settlement density was similar on glass, PDMS and P(4VP-r-BMA)$_{300k}$, but was considerably higher on P(4VP-r-BMA)$_{300k}$H6Br. The higher settlement is possibly due to electrostatic interactions between the settling organism and the cationic polymer. Although spore settlement was the highest on P(4VP-r-BMA)$_{300k}$ H6Br, the spores appeared damaged or moribund on these surfaces.

FIG. 16 shows the images of spores and 7 day old sporelings on glass, PDMS and P(4VP-r-BMA)$_{300k}$ H6Br. The pyridinium surfaces showed poor sporeling growth (FIG. 16f). Most surfaces showed increased sporeling removal with increasing water pressure (FIG. 17). Removal from P(4VP-r-BMA)$_{300k}$ H6Br was distinctly better than from glass or the unquaternized P(4VP-r-BMA)$_{300k}$ surfaces.

Navicula assays. The density of attached diatoms after gentle washing was similar on all surfaces (FIG. 18). Removal from P(4VP-r-BMA)$_{300k}$ H6Br was moderate, and higher compared to PDMS (FIG. 19). Examination 3 days post-inoculation showed a similar amount of growth on all surfaces. There was no difference in growth between the pyridinium surface and controls indicating that it was not toxic or leaching toxic materials. Observations at 24 hours, when cells were in log phase growth, showed that cells were motile on all surfaces.

Example 7

Representative Mers of the Polymers

FIG. 20 illustrates various mers of various embodiments of the invention wherein the mers can be selected in any combination in any order to prepare an antifouling polymer. The polymer shown in FIG. 20 merely illustrates the variety of mers that can be used in various embodiments and is not an actual polymer that has been prepared.

The group R2 that is a substituent of the quaternized nitrogen can be any of, for example, alkyl, perfluoroalkyl, semifluorinated alkyl, polyethylene glycol (PEG), or a PEGylated fluoroalkyl group. The variable R3 can be any suitable end-functional group, for example, hydrogen, a TEMPO derivative, or a substituted silyl group, such as trimethylsilyl or a dialkyl-partially fluorinated alkyl-silyl group, or other groups as discussed herein.

The specific lengths of alkyl, fluoroalkyl, and ethylene glycol groups shown in FIG. 20 are representative only and other chain lengths can be employed. The length of each mer substituent and/or quaternization group can be selected in order to achieve the desired physical properties of the antifouling coating being prepared.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An amphiphilic polymer comprising formula I:

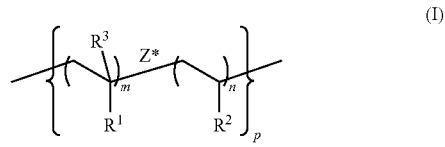

(I)

wherein
each R¹ is independently aryl or alkoxycarbonyl;
each R² is independently a pyridine or a pyridine(C₁-C₁₀)alkyl group, wherein at least 10% of the nitrogen atoms of the pyridine moieties are quaternized; wherein one or more quaternized pyridine-containing substituents are quaternized with (C₁-C₃₀)alkyl groups and one or more quaternized pyridine-containing substituents are quaternized with alkyl groups that include one or more ethylene glycol groups;
each R³ is independently hydrogen or methyl;
wherein any alkyl, aryl, or alkoxy is optionally substituted with one or more alkyl, alkoxy, halo, dialkylamino, trifluoromethyl, ethylene glycol, or perfluoroalkyl groups;
each m is about 5 to about 2000;
each n is about 5 to about 2,000;
p is about 5 to about 100; and
the dispersement of each individual m subunit and each individual n subunit on either side of z* is random and each individual m subunit and each individual n subunit occurs interchangeably with any other m or n subunit within the brackets of formula I; or the dispersement of each individual m subunit and each individual n subunit on either side of z* is that of a block copolymer.

2. The polymer of claim 1 wherein at least about 50% of the nitrogen atoms of the pyridine-containing substituents are quaternized with $(C_1-C_{30})$alkyl groups.

3. The polymer of claim 1 wherein and at least about 20% of the $(C_1-C_{30})$alkyl groups are at least partially fluorinated and one or more of the $(C_1-C_{30})$alkyl groups are $(C_6-C_{10})$perfluoroalkyl$(C_3-C_{10})$alkyl groups.

4. The polymer of claim 3 wherein one or more of the $(C_6-C_{10})$perfluoroalkyl-$(C_3-C_{10})$alkyl groups are 6-perfluorooctyl-1-hexyl groups.

5. The polymer of claim 1 wherein the molecular weight of the polymer is about 10 kDa to about 150 kDa and the polymer exhibits antifouling properties.

6. A bactericidal surface that includes a surface coating comprising the polymer of claim 1.

7. The bactericidal surface of claim 6 further comprising a base layer that comprises an elastomeric polymer.

8. The polymer of claim 1 wherein each $R^1$ is phenyl or butoxycarbonyl.

9. The polymer of claim 1 wherein each $R^1$ is phenyl and the polymer is a block copolymer.

10. The polymer of claim 1 wherein each $R^1$ is butoxycarbonyl and the polymer is a random copolymer.

11. The polymer of claim 1 wherein each $R^2$ is 4-pyridine.

12. The polymer of claim 11 wherein the 4-pyridine groups are at least 20% quaternized with partially fluorinated $(C_1-C_{30})$alkyl groups.

13. The polymer of claim 11 wherein the 4-pyridine groups are at least 20% quaternized with non-fluorinated $(C_1-C_{30})$alkyl groups.

14. The polymer of claim 1 wherein at least about 10% of the $(C_1-C_{30})$alkyl groups are at least partially fluorinated.

15. The polymer of claim 1 wherein m, n, and p are selected such that the molecular weight of the polymer is about 5 kDa to about 500 kDa.

16. A coating comprising the polymer of claim 1 in combination with an elastomeric polymer sublayer.

17. The polymer of claim 1 wherein one or more of the alkyl groups that include one or more ethylene glycol groups is a moiety of formula Z:

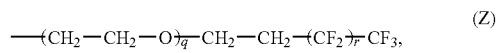

wherein each q is independently 1 to about 25; each r is independently 0 to about 18.

* * * * *